United States Patent [19]

Juby

[11] 4,122,274

[45] Oct. 24, 1978

[54] 3-TETRAZOLO-5,6,7,8-SUBSTITUTED-PYRIDO[1,2-a]PYRIMIDIN-4-ONES

[75] Inventor: Peter Frederick Juby, Jamesville, N.Y.

[73] Assignee: Bristol-Myers Company, New York, N.Y.

[21] Appl. No.: 800,264

[22] Filed: May 25, 1977

[51] Int. Cl.$^2$ ............... C07D 471/04; A61K 33/505
[52] U.S. Cl. ..................... 544/282; 544/249; 544/250; 544/116
[58] Field of Search ............ 260/256.4 F, 256.5 R

[56] References Cited

U.S. PATENT DOCUMENTS

| | | | |
|---|---|---|---|
| 3,072,485 | 1/1963 | Reynolds et al. | 96/115 |
| 3,585,198 | 6/1971 | Meszaros et al. | 260/251 |
| 3,929,787 | 12/1975 | Yale | 260/251 A |
| 3,960,847 | 6/1976 | Yale | 260/240 K |
| 3,960,863 | 6/1976 | Sato et al. | 260/256.4 F |
| 4,017,625 | 4/1977 | Kadin | 260/256.4 F |

OTHER PUBLICATIONS

Cox, et al., "Advances in Drug Res.", vol. 5, 1970, pp. 115–196.
Landquist, "J. Chem. Soc.", (C), 1971, pp. 2735–2738.
Antaki, "J.A.C.S.", vol. 80, 1958, pp. 3066–3069.
Adams, et al., "J.A.C.S.", vol. 74, 1952, pp. 5491–5497.
Shur, et al., "J. Org. Chem.", vol. 33, 1968, pp. 3015–3020.
Meszaros, et al., "Arzneim.-Forsch", vol. 22, 1972, pp. 815–829.
Meszaros, et al., "Tetrahedron Letters", No. 12, 1975, pp. 1019–1020.

*Primary Examiner*—Donald G. Daus
*Assistant Examiner*—James H. Turnipseed
*Attorney, Agent, or Firm*—David M. Morse

[57] ABSTRACT

A novel series of optionally substituted 3-(1H-tetrazol-5-yl)-4H-pyrido[1,2-a]pyrimidin-4-ones is provided for use as inhibitors of allergic reactions. The compounds exhibit antiallergy activity by both oral and parenteral routes of administration.

27 Claims, No Drawings

3-TETRAZOLO-5,6,7,8-SUBSTITUTED-PYRIDO[1,2-A]PYRIMIDIN-4-ONES

BACKGROUND OF THE INVENTION

1. Field of the Invention

This invention relates to optionally substituted 3-(1H-tetrazol-5-yl)-4H-pyrido[1,2-a]pyrimidin-4-one derivatives and to their use as inhibitors of allergic reactions.

2. Description of the Prior Art

Various medicinal agents have been employed in the treatment of allergic reactions such as bronchial asthma and allergic rhinitis which are believed to result mainly from antigen-antibody interaction. With respect to bronchial asthma, one of the most serious of these allergically-mediated diseases, bronchodilators such as theophylline, isoproterenol, epinephrine and atropine are used primarily in providing symptomatic relief. These agents, however, have undesirable side effects, e.g. cardiac stimulation and gastrointestinal distress.

With the recent introduction of disodium cromoglycate described by J. S. G. Cox, et al. in *Adv. in Drug Res.*, 5, 115–196 (1970), the physician has been provided with an agent which, when administered to asthmatic patients prior to inhalation of specific antigens, inhibits the release of mediators, e.g. histamine and SRS-A (slow-reacting-substance of anaphylaxis), believed to be responsible for the asthmatic response. While making possible a prophylactic treatment for bronchial asthma without cardiovascular side effects and thus representing a significant advance, disodium cromoglycate suffers from a major disadvantage in that it is not orally absorbed and must be administered by inhalation.

With respect to the compounds of the present invention, no examples of tetrazol-5-yl-4H-pyrido[1,2-a]pyrimidin-4-ones have been found in the literature. Numerous examples of the pyrido[1,2-a]pyrimidine ring system, however, are known, including many 4-oxo derivatives.

U.S. Pat. No. 3,585,198 reviews some of the literature of the pyrido[1,2-a]pyrimidines and discloses compounds of the general formula

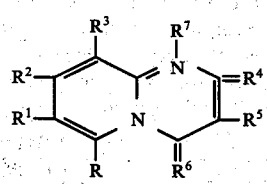

where R, $R^1$, $R^2$ and $R^3$ may be hydrogen, alkyl, alkoxy, halogen, nitro or amino, $R^4$ is hydrogen, alkyl, aralkyl, aryl, =O, alkoxy, halogen or hydroxy, $R^5$ is hydrogen, halogen, a —$CH_2$—OH group, a carboxylic acid or carboxylic acid derivative group, $R^6$ is hydrogen, alkyl, aralkyl, aryl, =O, alkoxy, halogen, or hydroxy and $R^7$ is hydrogen, alkyl, aryl or alkyl. The disclosed compounds are said to exhibit analgesic, antipyretic and narcosis potentiating effects.

U.S. Pat. No. 3,929,787 discloses 2-aryl-9-alkyl-4H-pyrido[1,2-a]pyrimidin-4-one compounds of the formula

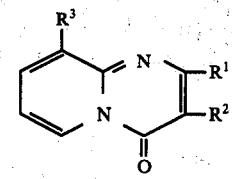

where $R^1$ is phenyl or substituted phenyl, $R^2$ is hydrogen or alkyl and $R^3$ is alkyl. These compounds are reported to be intermediates in preparing the corresponding 6,7,8,9-tetrahydro derivatives which possess central nervous system depressant activity.

U.S. Pat. No. 3,072,485 discloses inter alia compounds of the formula

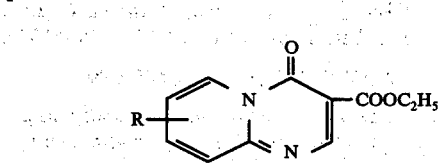

where R is hydrogen, bromo, chloro, iodo or methyl. The compounds are used as photographic sensitizers.

Compounds of the formula

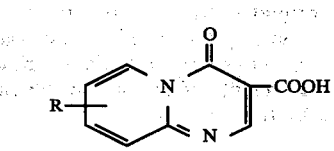

where R is hydrogen, 9-methyl or 8-methyl are disclosed by Okamoto, et al. in Chem. Pharm. Bull. (Tokyo), 22, 243 (1974). No pharmacological utility for the compounds is indicated.

U.S. Pat. No. 3,960,847 discloses inter alia 9-substituted pyrido[1,2-a]pyrimidines of the formula

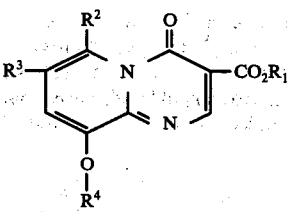

where $R^1$ is hydrogen or $C_1$–$C_4$ alkyl, $R^2$ and $R^3$ are hydrogen, $C_1$–$C_4$ alkyl, $CF_3$, F, Cl or Br and $R^4$ is inter alia an alkyl radical substituted by a phenyl or substituted phenyl radical, such as benzyl, substituted benzyl, phenethyl or substituted phenethyl. The compounds are said to have both central nervous system and hypotensive activities.

J. K. Landquist has described in *J. Chem. Soc.* (C), 2735 (1971) the preparation of the carboxamide compound of the formula

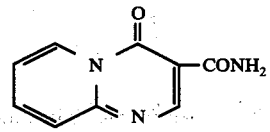

by treatment of the corresponding ethyl ester with ammonium hydroxide in ethanol. No pharmacological utility is given for the disclosed carboxamide.

Preparation of the cyano derivatives of the formula

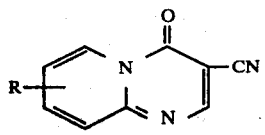

where R is hydrogen, 6-methyl or 9-methyl is disclosed in *J. Amer. Chem. Soc.*, 80, 3066 (1958). No pharmacological utility for the compounds is indicated.

Other references to the chemistry of pyrido[1,2-a]pyrimidinones include *J. Amer. Chem. Soc.*, 74, 5491 (1952), *J. Org. Chem.*, 33, 3015 (1968), *Arzneim.-Forsch.*, 22, 815 (1972) and *Tetrahedron Lett.*, (12), 1019 (1975).

SUMMARY OF THE INVENTION

This invention relates to new therapeutically useful 3-(1H-tetrazol-5-yl)-4H-pyrido[1,2-a]pyrimidin-4-one derivatives, to processes for their preparation, to pharmaceutical compositions containing them and to methods for treating allergically-mediated diseases in mammals by administration of such derivatives or pharmaceutical compositions thereof. The compounds and compositions provided by the present invention are particularly valuable in the prophylactic treatment of allergic bronchial asthma by oral administration.

The antiallergy agents of the present invention may be represented by the formula

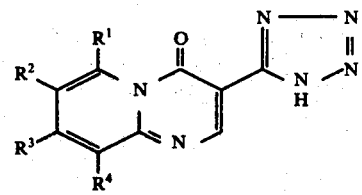

wherein $R^1$, $R^2$, $R^3$ and $R^4$ which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, -O-(lower)alkenyl,

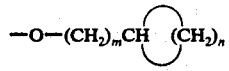

in which $m$ is 0 or an integer from 1 to 6 and $n$ is an integer from 2 to 7, $-OCH_2(CH_2)_xO(CH_2)_yCH_3$ in which $x$ and $y$ are each independently 0 or an integer from 1 to 6, $CF_3$, hydroxy, hydroxymethyl, (lower)alkylthio, amino, nitro,

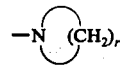

in which $r$ is 4 or 5,

(lower)alkylamino, di(lower)alkylamino, carboxyl, $-CO_2$-(lower)alkyl, phenyl, phenyl substituted by one or two (lower)alkyl, (lower)alkoxy or halogen radicals, benzyl, (lower)alkylsulfinyl, $R^c$—CO— in which $R^c$ is (lower)alkyl, $R^c$—COO— in which $R^c$ is (lower)alkyl, $-O(CH_2)_kOH$ in which $k$ is an integer from 2 to 6,

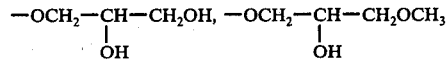

or $-OCH_2C_6H_5$, or $R^2$ and $R^3$ or $R^3$ and $R^4$ when taken together are methylenedioxy or

in which $n$ is 3, 4 or 5, and pharmaceutically acceptable salts thereof.

The $R^1$, $R^2$, $R^3$ and $R^4$ substituent groups disclosed above may be further defined as follows:

(a) Halogen includes chlorine, bromine, fluorine and iodine;

(b) (Lower)alkyl includes both straight and branched chain saturated aliphatic hydrocarbon radicals having from 1-6 carbon atoms inclusive, e.g. methyl, ethyl, n-propyl, isopropyl, n-butyl, isobutyl, sec-butyl, tert-butyl, n-pentyl, isopentyl, n-hexyl, etc.;

(c) (Lower)alkenyl includes straight or branched unsaturated aliphatic hydrocarbon radicals containing one double bond and having from 2-6 carbon atoms inclusive, e.g. vinyl, allyl, isopropenyl, 2- or 3-methallyl or 3-butenyl;

(d) (Lower)alkoxy includes $C_1$-$C_6$ alkoxy radicals, the alkyl portion of such radicals being defined as in (b) above. Examples include methoxy, ethoxy, n-propoxy, isopropoxy, n-butoxy, isobutoxy, sec-butoxy, n-pentyloxy, isopentyloxy, n-hexyloxy, etc.;

(e) —O-(Lowr)alkenyl groups include radicals in which the alkenyl portion is as defined above in (c), e.g. vinyloxy, allyloxy or isopropenyloxy;

(f)

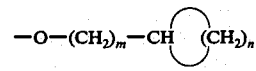

includes cyclo(lower)alkyloxy and cyclo(lower)alkyl-($C_1$-$C_6$)alkyloxy groups in which the cycloalkyl ring contains from 3 to 8 carbon atoms, preferably 3-6 carbon atoms. Examples of such groups are cyclopropyloxy, cyclobutyloxy, cyclopentyloxy, cyclohexyloxy, cycloheptyloxy, cyclopropylmethyloxy, cyclopropylethyloxy, cyclobutylmethyloxy, cyclobutylethyloxy, cyclopentylmethyloxy, cyclohexylmethyloxy, cyclohexylethyloxy and cyclohexylpropyloxy;

(g) $-O-CH_2(CH_2)_xO(CH_2)_yCH_3$ includes radicals such as $-OCH_2OCH_3$, $-OCH_2CH_2OCH_3$, $-OCH_2CH_2OCH_2CH_3$, $-OCH_2OCH_2CH_3$ and $-OCH_2CH_2OCH_2CH_3$;

(h) (Lower)alkylthio includes $C_1$-$C_6$ alkylthio radicals in which the alkyl portion is as defined above in (b). Examples of such groups are methylthio, ethylthio, n-propylthio and n-butylthio;

(i) (Lower)alkylamino includes $C_1$-$C_6$ alkylamino radicals in which alkyl is as defined in (b). Examples of such groups are methylamino, ethylamino, propylamino and butylamino;

(j) Di(lower)alkylamino includes di $C_1$-$C_6$ alkylamino radicals in which alkyl is as defined above in (b). Examples of such groups are dimethylamino and diethylamino;

(k) —CO$_2$-(Lower)alkyl includes ester radicals in which the alkyl moiety is as defined above in (b), e.g. carbomethoxy, carbethoxy, carbopropoxy and carbobutoxy;

(l) (Lower)alkylsulfinyl represents radicals of the formula $$-\overset{O}{\underset{\|}{S}}-\text{(lower)alkyl}$$

in which the alkyl portion is as defined above in (b). Examples of such radicals include methylsulfinyl, ethylsulfinyl, n-propylsulfinyl, isopropylsulfinyl, n-butylsulfinyl, sec-butylsulfinyl, isobutylsulfinyl, t-butylsulfinyl, n-pentylsulfinyl and n-hexylsulfinyl. The most preferred alkylsulfinyl group is methylsulfinyl;

(m) Acyl includes radicals of the type R$^c$—CO— where R$^c$ is an aliphatic, cycloaliphatic, aromatic or araliphatic hydrocarbon radical or a heterocyclic-aliphatic radical, e.g. CH$_3$CO—, C$_2$H$_5$CO—, C$_3$H$_7$CO—, C$_6$H$_5$CO—, C$_6$H$_5$CH$_2$CO—,

[structures: thiophene-CH$_2$CO— and cyclopropyl CH—CO—]

Preferred acyl groups are those in which R$^c$ is alkyl as defined in (b);

(n) Acyloxy includes radicals of the type R$^c$—COO— in which R$^c$ is as defined above in connection with acyl and is preferably C$_1$-C$_6$ alkyl. Examples are CH$_3$COO—, C$_2$H$_5$COO—, C$_3$H$_7$COO—, C$_6$H$_5$CH$_2$COO— and C$_6$H$_5$COO-;

(o)

$$-\text{N}\overbrace{(CH_2)_r}$$

includes pyrrolidino and piperidino;

(p) Cyclo(lower)alkyl means cycloalkyl radicals having from 3-6 carbon atoms. Examples include cyclopropyl, cyclobutyl, cyclohexyl, etc.;

(q) R$^2$ and R$^3$ or R$^3$ and R$^4$ taken together may be $$\overbrace{(CH_2)_n}$$

which represents a saturated five, six or seven membered monocyclic hydrocarbon radical fused to the A ring of the pyrido[1,2-a]pyrimidine ring system, e.g.

[structure with n = 4]

or

[structure with n = 3];

(r) (Lower)alkynyl represents straight or branched unsaturated aliphatic hydrocarbon radicals containing one triple bond and having from 2 to 6 carbon atoms inclusive, e.g. ethynyl, propargyl, butynyl, pentynyl or hexynyl;

(s) (Lower)alkoxy(lower)alkyl represents radicals where the (lower)alkoxy and (lower)alkyl portions are as defined above in (d) and (b), respectively, e.g. methoxymethyl, methoxyethyl, ethoxymethyl, ethoxyethyl, methoxypropyl, etc.; and (t) Cyclo(lower)alkyl(lower)alkyl represents radicals in which the cyclo(lower)alkyl and (lower)alkyl portions are as defined above in (p) and (b) respectively, e.g. cyclopropylmethyl, cyclopropylethyl, cyclopropylbutyl, cyclohexylmethyl, cylohexylethyl, etc.

A preferred embodiment of the present invention comprises the compounds of formula I wherein R$^1$, R$^2$, R$^3$ and R$^4$ which may be the same or different are each hydrogen, (lower)alkyl, (lower)alkenyl, (lower)alkoxy, hydroxy, carboxy, (lower)alkylthio, halogen, CF$_3$, amino, (lower)alkylamino, di(lower)alkylamino, phenyl or benzyl.

A more preferred embodiment of the present invention comprises the compounds of the formula

[structure I']

wherein R$^1$, R$^2$ and R$^3$ which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O-(lower)alkenyl, $$-\text{O}-(CH_2)_m\text{CH}\overbrace{(CH_2)_n}$$

in which m is 0 or an integer from 1 to 6 and n is an integer from 2 to 7, —OCH$_2$(CH$_2$)$_x$O(CH$_2$)$_y$CH$_3$ in which x and y are each independently 0 or an integer from 1 to 6, CF$_3$, hydroxy, hydroxymethyl, (lower)alkylthio, amino, nitro, $$-\text{N}\overbrace{(CH_2)_r}$$

in which r is 4 or 5,

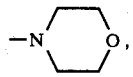

(lower)alkylamino, di(lower)alkylamino, carboxyl, —CO₂-(lower)alkyl, phenyl, phenyl substituted by one or two (lower)alkyl, (lower)alkoxy or halogen radicals, benzyl, (lower)alkylsulfinyl, R$^c$—CO— in which R$^c$ is (lower)alkyl, R$^c$—COO— in which R$^c$ is (lower)alkyl, —O(CH$_2$)$_k$OH in which $k$ is an integer from 2 to 6,

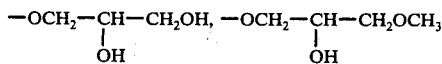

or —OCH$_2$C$_6$H$_5$, or wherein any two of R$^1$, R$^2$ and R$^3$ at positions 7 and 8 or 8 and 9 of the pyrido[1,2-a]pyrimidine ring system when taken together represent methylenedioxy or

in which $n$ is 3, 4 or 5, and the pharmaceutically acceptable salts thereof. Within this group of compounds, a preferred subgroup comprises those compounds where R$^1$, R$^2$ and R$^3$ are each independently hydrogen, (lower)alkyl, (lower)alkenyl, (lower)alkoxy, hydroxy, carboxy, (lower)alkylthio, halogen, CF$_3$, amino, (lower)alkylamino, di(lower)alkylamino, phenyl or benzyl. The R$^1$, R$^2$ and R$^3$ substituents of compound I' may be located at any of positions 6, 7, 8 or 9 of the pyrido[1,2-a]pyrimidine ring system as numbered above.

Another more preferred embodiment of the present invention comprises the compounds of the formula

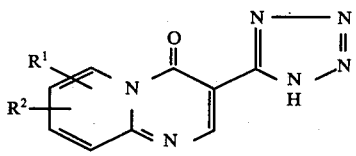

wherein R$^1$ and R$^2$ which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O-(lower)alkenyl,

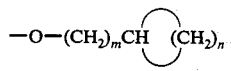

in which $m$ is 0 or an integer from 1 to 6 and $n$ is an integer from 2 to 7, —OCH$_2$(CH$_2$)$_x$O(CH$_2$)$_y$CH$_3$ in which $x$ and $y$ are each independently 0 or an integer from 1 to 6, CF$_3$, hydroxy, hydroxymethyl, (lower)alkylthio, amino, nitro,

in which $r$ is 4 or 5,

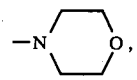

(lower)alkylamino, di(lower)alkylamino, carboxyl, —CO₂-(lower)alkyl, phenyl, phenyl substituted by one or two (lower)alkyl, (lower)alkoxy or halogen radicals, benzyl, (lower)alkylsulfinyl, R$^c$—CO— in which R$^c$ is (lower)alkyl, R$^c$—COO— in which R$^c$ is (lower)alkyl, —O(CH$_2$)$_k$OH in which $k$ is an integer from 2 to 6,

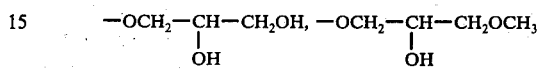

or —OCH$_2$C$_6$H$_5$, or R$^1$ and R$^2$ when taken together at positions 7 and 8 or 8 and 9 of the pyrido[1,2-a]pyrimidine ring system are methylenedioxy or

in which $n$ is 3, 4 or 5, and the pharmaceutically acceptable salts thereof. Within this group of compounds, a preferred subgroup comprises those compounds wherein R$^1$ and R$^2$ are each independently hydrogen, (lower)alkyl, (lower)alkenyl, (lower)alkoxy, hydroxy, carboxy, (lower)alkylthio, halogen, CF$_3$, amino, (lower)alkylamino, di(lower)alkylamino, phenyl or benzyl. The R$^1$ and R$^2$ substituents of compound I'' may be located at any of positions 6, 7, 8 or 9 of the pyrido[1,2-a]pyrimidine ring system.

Another more preferred embodiment of the present invention comprises the compounds of the formula

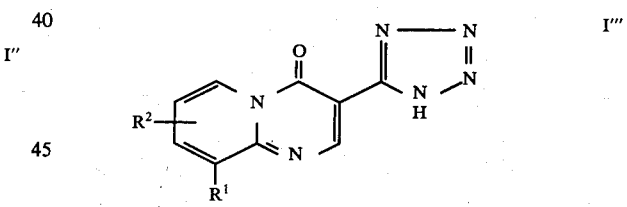

wherein R$^1$ and R$^2$ which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O-(lower)alkenyl,

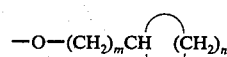

in which $m$ is 0 or an integer from 1 to 6 and $n$ is an integer from 2 to 7, —OCH$_2$(CH$_2$)$_x$O(CH$_2$)$_y$CH$_3$ in which $x$ and $y$ are each independently 0 or an integer from 1 to 6, CF$_3$, hydroxy, hydroxymethyl, (lower)alkylthio, amino, nitro,

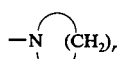

in which $r$ is 4 or 5,

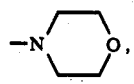

(lower)alkylamino, di(lower)alkylamino, carboxyl, —CO₂-(lower)alkyl, phenyl, phenyl substituted by one or two (lower)alkyl, (lower)alkoxy or halogen radicals, benzyl, (lower)alkylsulfinyl, R$^c$—CO— in which R$^c$ is (lower)alkyl, R$^c$—COO— in which R$^c$ is (lower)alkyl, —O(CH₂)$_k$OH in which $k$ is $n$ integer from 2 to 6,

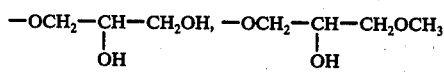

or —OCH₂C₆H₅, or R¹ and R² when taken together at positions 8 and 9 of the pyrido[1,2-a]pyrimidine ring system are methylenedioxy or

in which $n$ is 3, 4 or 5, and the pharmaceutically acceptable salts thereof. Within this group of compounds, a preferred subgroup comprises those compounds wherein R¹ and R² are each independently hydrogen, (lower)alkyl, (lower)alkenyl, (lower)alkoxy, hydroxy, carboxy, (lower)alkylthio, halogen, CF₃, amino, (lower)alkylamino, di(lower)alkylamino, phenyl or benzyl. The R² substituent of compound I''' may be located at any of positions 6, 7 or 8 of the pyrido[1,2-a]pyrimidine ring system.

Another more preferred embodiment of the present invention comprises the compounds of the formula

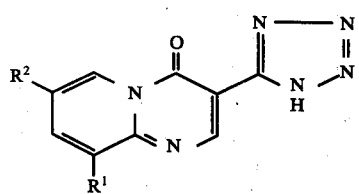

wherein R¹ and R² which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, -O-(lower)alkenyl,

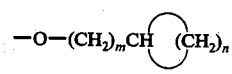

in which $m$ is 0 or an integer from 1 to 6 and $n$ is an integer from 2 to 7, —OCH₂(CH₂)$_x$O(CH₂)$_y$CH₃ in which $x$ and $y$ are each independently 0 or an integer from 1 to 6, CF₃, hydroxy, hydroxymethyl, (lower)alkylthio, amino, nitro,

in which $r$ is 4 or 5,

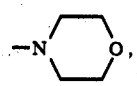

(lower)alkylamino, di(lower)alkylamino, carboxyl, —CO₂-(lower)alkyl, phenyl, phenyl substituted by one or two (lower)alkyl, (lower)alkoxy or halogen radicals, benzyl, (lower)alkylsulfinyl, R$^c$—CO— in which R$^c$ is (lower)alkyl, R$^c$—COO— in which R$^c$ is (lower)alkyl, —O(CH₂)$_k$OH in which $k$ is an integer from 2 to 6,

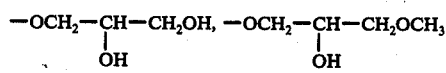

or —OCH₂C₆H₅, and the pharmaceutically acceptable salts thereof. Within this group of compounds, a preferred subgroup comprises those compounds wherein R¹ and R² are each independently hydrogen, (lower)alkyl, (lower)alkenyl, (lower)alkoxy, hydroxy, carboxy, (lower)alkylthio, halogen, CF₃, amino, (lower)alkylamino, di(lower)alkylamino, phenyl or benzyl.

Another more preferred embodiment of the present invention comprises the compounds of the formula

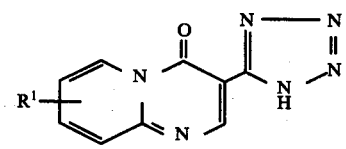

wherein R¹ is hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O-(lower)alkenyl,

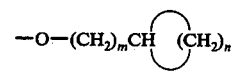

in which $m$ is 0 or an integer from 1 to 6 and $n$ is an integer from 2 to 7, —OCH₂(CH₂)$_x$O(CH₂)$_y$CH₃ in which $x$ and $y$ are each independently 0 or an integer from 1 to 6, CF₃, hydroxy, hydroxymethyl, (lower)alkylthio, amino, nitro,

in which $r$ is 4 or 5,

(lower)alkylamino, di(lower)alkylamino, carboxyl, —CO₂-(lower)alkyl, phenyl, phenyl substituted by one or two (lower)alkyl, (lower)alkoxy or halogen radicals, benzyl, (lower)alkylsulfinyl, R$^c$—CO— in which R$^c$ is (lower)alkyl, R$^c$—COO— in which R$^c$ is (lower)alkyl, —O(CH₂)$_k$OH in which $k$ is an integer from 2 to 6,

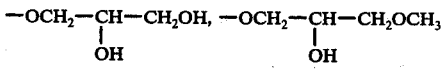

or —OCH$_2$C$_6$H$_5$, and the pharmaceutically acceptable salts thereof. Within this group of compounds, a preferred subgroup comprises the compounds wherein R$^1$ represents hydrogen, (lower)alkyl, (lower)alkenyl, (lower)alkoxy, hydroxy, carboxy, (lower)alkylthio, halogen, CF$_3$, amino, (lower)alkylamino, di(lower)alkylamino, phenyl or benzyl.

While the R$^1$ substituents in the compounds of formula I'''' may be located at any of positions 6, 7, 8 or 9 of the pyrido[1,2-a]pyrimidine ring system, the 7- and 9-substituted compounds are preferred. The most preferred monosubstituted compounds are those having the substituent at the 9-position.

Since the compounds of this invention are amphoteric in nature, they can be converted to salts of either acids or bases by treating said compounds with a substantially equimolar amount of a chosen acid or base in an aqueous solution or in a suitable organic solvent such as methanol or ethanol. When such salts are to be used for human consumption, the acids or bases which are used to prepare the pharmaceutically acceptable salts must, of course, be those which necessarily form nontoxic salts. Examples of suitable acids include hydrochloric, hydrobromic, hydroiodic, nitric, sulfuric, phosphoric, acetic, lactic, citric, tartaric, oxalic, succinic, maleic, gluconic, ascorbic and p-toluene sulfonic. Pharmaceutically acceptable salts may be formed from such bases as ammonia, organic amines and metal salts, e.g. metal salts containing sodium, potassium, calcium, magnesium, barium and aluminum cations. Representative of such bases are ammonia, primary amines such as n-propylamine, n-butylamine, ethanolamine, ethylenediamine, cyclohexylamine, benzylamine, ethylamine, octylamine or tris(hydroxymethyl)aminomethane, secondary amines such as diethanolamine, tertiary amines such as triethanolamine, N-methylpyrrolidine, N-methylmorpholine, or 1,5-diazabicyclo[4,3,0]-5-nonene and metal compounds such as sodium hydroxide, potassium hydroxide, ammonium hydroxide, sodium ethoxide, potassium methoxide, magnesium hydroxide, calcium hydroxide or aluminum hydroxide.

Those skilled in the art will appreciate that the compounds represented by formulae I — I''''' contain a tautomeric hydrogen atom and the compounds are thus capable of existing in the 1H-tetrazol-5-yl form (see formula I$_a$ below) and the 2H-tetrazol-5-yl form (formula I$_b$ below).

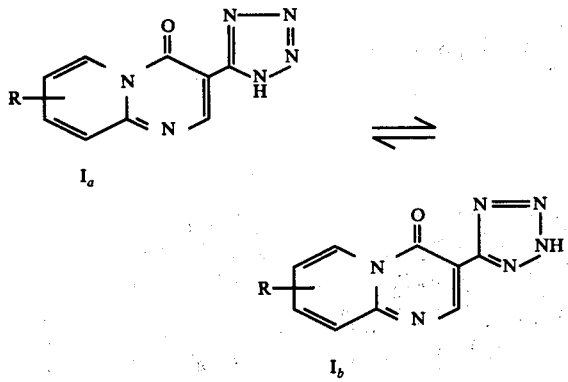

This invention embraces both forms, but for the sake of convenience, structure I$_a$ has been arbitrarily selected to describe the present compounds.

The compounds of the present invention may be prepared by the methods set forth below.

One preferred method comprises reacting a nitrile of the formula

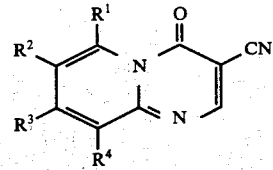

(wherein R$^1$, R$^2$, R$^3$ and R$^4$ are defined as above in reference to formula I) with an azide salt selected from the group consisting of ammonium, substituted ammonium and sodium and lithium azide in an inert organic solvent. The nitrile II and azide salt may be used in approximately equimolar amounts. The general conversion of nitriles to tetrazoles is described by W. G. Finnegan, et al. in *J. Am. Chem. Soc.*, 80, 3908 (1958). Examples of suitable azide salts for this process are provided by Finnegan in the above-mentioned reference and include azides such as NaN$_3$, LiN$_3$, NH$_4$N$_3$, (n-C$_4$H$_9$)$_2$NH$_2$N$_3$, C$_6$H$_5$NH$_3$N$_3$ and (CH$_3$)$_4$NN$_3$. The azide salt may be added directly or may be generated in situ, e.g. by double decomposition reactions of sodium azide and an appropriate chloride salt such as LiCl, NH$_4$Cl, (CH$_3$)$_4$NCl, etc. While the condensation reaction proceeds over a wide temperature range, it is preferred in order to minimize reaction times to use elevated temperatures, e.g. from about 100° C. up to the reflux temperature of the solvent system. The inert organic solvent may in general be any solvent having good solvent power for the azide salt and which is chemically inert. Examples of preferred solvents are dimethylformamide, dimethylacetamide, dimethylsulfoxide and hexamethylphosphoramide. The most preferred solvent is dimethylformamide. The condensation reaction is found to be subject to general acid catalysis and yields are improved by addition of such reagents as hydrazoic acid, amine hydroazides and Lewis acids such as BF$_3$ to the sodium azide. At the completion of the reaction, the tetrazole product may be recovered from the reaction mixture by removing the solvent, diluting the residue with water and then acidifying the mixture to give the desired product of formula I. The product may be further purified by recrystallization and optionally converted to a pharmaceutically acceptable salt thereof as described above. Following condensation, products of formula I may, if desired, be further reacted by methods known per se to convert one or more R$^1$, R$^2$, R$^3$ or R$^4$ substituent groups to other substituent groups within the scope of formula I. Thus, for example, a compound of formula I having a nitro substituent may be subjected to catalytic hydrogenation to give the corresponding amino-substituted compound or a compound having an amino substituent may be alkylated to give the corresponding (lower)alkylamino- or di(lower)alkylamino-substituted compound.

An alternative and preferred variation of the above procedure involves condensing the nitrile starting material II with aluminum azide in tetrahydrofuran followed by an acidification recovery step as described above. The reaction may conveniently be carried out by reacting nitrile II with aluminum chloride and sodium azide in molar proportions of about 1:1:3, respectively. While the temperature for this reaction is not critical, advantageous results have been obtained at the reflux temperature of the solvent.

Another alternative variation of the above procedure comprises heating the desired nitrile compound II with either hydrazoic acid in an inert organic solvent such as benzene, xylene or toluene or with sodium azide and acetic acid in butanol. In this procedure an acidification step is not required to recover the desired end-product.

An alternative and most preferred procedure for preparing the compounds of formula I comprises reacting an acrylate intermediate of the formula

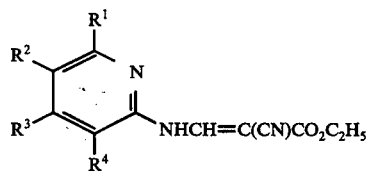

VI (wherein $R^1$, $R^2$, $R^3$ and $R^4$ are as defined above in reference to formula I) with aluminum azide in tetrahydrofuran. The preferred reaction conditions, i.e. molar ratios and temperature ranges, are as described above in connection with the nitrile to tetrazole conversion with $Al(N_3)_3$. The product of formula I may be conveniently recovered from the reaction mixture by addition of sufficient water followed by acidification to effect precipitation of the desired compound I. The tetrazole product I may, if desired, be subsequently converted as discussed above to a pharmaceutically acceptable salt or to another product of formula I having different $R^1$, $R^2$, $R^3$ or $R^4$ substituents.

Another preferred procedure for preparing the compounds of formula I comprises reacting a 2-aminopyridine of the formula

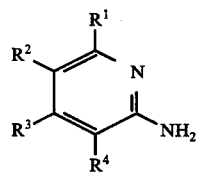

VII (wherein $R^1$, $R^2$, $R^3$ and $R^4$ are as defined above in reference to formula I) with ethyl ethoxymethylenecyanoacetate of the formula $$C_2H_5OCH=C(CN)CO_2C_2H_5 \quad VIII$$

and aluminum azide in tetrahydrofuran. Approximately equimolar quantities of the three reactants are used, and the aluminum azide may be conveniently prepared in situ by reaction of sodium azide and aluminum chloride in molar proportions of about 3:1, respectively. For best results, the reaction is carried out at the reflux temperature of the solvent. At the conclusion of the reaction, the desired product can be recovered by addition of sufficient water followed by acidification to precipitate compound I from the reaction mixture. The product may as described above be further reacted to produce a pharmaceutically acceptable salt thereof or another product of formula I having different $R^1$, $R^2$, $R^3$ or $R^4$ substituents.

The above process is a preferred embodiment of the present invention since it enables compound I to be prepared directly from the basic 2-aminopyridine and ethyl ethoxymethylenecyanoacetate starting materials without the necessity of first preparing and isolating one or more intermediates required for the alternative methods described above.

The nitrile starting materials of formula II may be prepared by known reaction routes. One reaction scheme is indicated below:

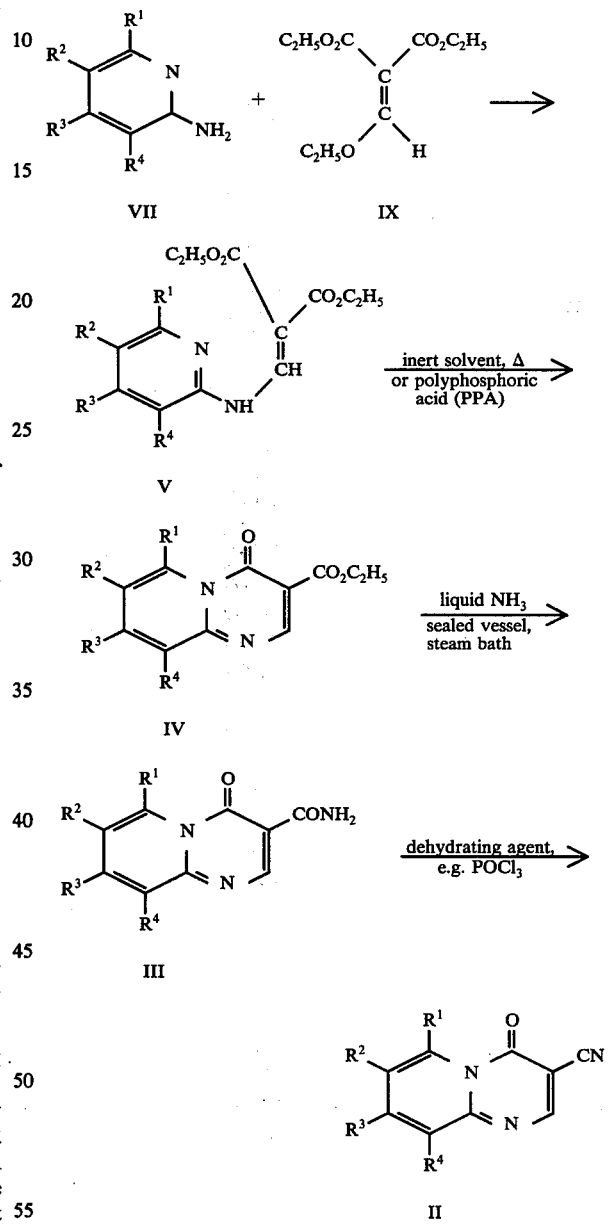

The 2-aminopyridine starting materials of formula VII are known compounds or are prepared by methods well known in the art.

Condensation of 2-aminopyridines (formula VII) with diethyl ethoxymethylenemalonate (formula IX) to produce the esters of formula IV is well-documented in the literature (see prior art section above and, in particular, U.S. Pat. No. 3,585,198, *J. Chem. Soc.* (C), 2735 (1971), *J. Org. Chem.*, 33, 3015 (1968), *Arzneim.-Forsch.*, 22, 815 (1972) and *J. Amer. Chem. Soc.*, 70, 3348 (1948), and the references cited therein).

Amide intermediates of formula III may be obtained by treatment of the esters of formula IV with liquid ammonia, ammonium hydroxide or a solution of ammonia in a (lower)alkanol (e.g. methanol or ethanol) optionally containing sodium methoxide as a catalyst. The reaction is conveniently carried out in a sealed vessel at steam bath temperature. When concentrated ammonium hydroxide is used, good results have also been achieved at room temperature for 1 to 2 days without the necessity of either heat or a sealed vessel.

The amide intermediate of formula III may be converted to the nitriles of formula II by use of a dehydrating agent such as phosphorus pentoxide, thionyl chloride, p-toluenesulfonyl chloride:pyridine or, most preferably, phosphorus oxychloride. Dehydration is accomplished at elevated temperatures, most preferably under reflux conditions.

The acrylate starting materials of formula VI may be prepared by condensing approximately equimolar amounts of a 2-aminopyridine compound of formula VII with ethyl ethoxymethylenecyanoacetate in the presence or absence of an inert organic solvent, e.g. an aromatic hydrocarbon such as toluene. The reaction is preferably carried out at elevated temperatures, e.g. 100° C. Some examples of the acrylates of formula VI (i.e. when the pyridine ring is unsubstituted or substituted at the 3-, 4- or 6-position by methyl) are disclosed by Antaki in *J. Amer. Chem. Soc.*, 80, 3066 (1958) and by Nishigaki, et al. in *J. Heterocycl. Chem.*, 8, 759 (1971).

In using the above-described processes to prepare compounds of formula I in which $R^1$, $R^2$, $R^3$ or $R^4$ contain free hydroxy, amino or carboxyl groups, it is of course understood that such groups will be protected by suitable known protecting groups during the reaction steps beginning with the basic 2-aminopyridine starting materials through the formation of the final tetrazoles. The protecting group(s) may then be removed by methods known per se to give the desired products having the unprotected substituent groups. Amino-substituted compounds may be prepared from the corresponding nitro-substituted product by catalytic hydrogenation. In preparing compounds of formula I where $R^1$, $R^2$, $R^3$ or $R^4$ are (lower)alkylamino or di(lower)alkylamino, the corresponding amino-substituted compound may first be prepared and then alkylated. Alternatively, the dialkylamino-substituted compounds can be prepared directly from the appropriate 2-amino-pyridine starting material.

In another aspect of the present invention, there is provided a method of inhibiting or preventing the symptoms of an allergic reaction such as allergic bronchial asthma or allergic rhinitis in a mammal susceptible to such a reaction which comprises administering to said mammal a prophylactically effective dose of a compound of formula I or a pharmaceutically acceptable salt thereof.

The compounds of the present invention may be administered either as individual therapeutic agents or as mixtures with other therapeutic agents. They may be administered alone but are generally administered in the form of pharmaceutical compositions, i.e. mixtures of the active agents with suitable pharmaceutical carriers or diluents. Examples of such compositions include tablets, lozenges, capsules, powders, aerosol sprays, aqueous or oily suspensions, syrups, elixers and aqueous solutions. The compounds are preferably administered orally, but may also be administered by inhalation, injection, instillation or by implantation for controlled drug release from a solid carrier reservoir.

The nature of the pharmaceutical composition and the pharmaceutical carrier or diluent will, of course, depend on the desired route of administration. For example, oral compositions may be in the form of tablets or capsules and may contain conventional excipients such as binding agents (e.g. syrup, acacia, gelatin, sorbitol, tragacanth or polyvinylpyrrolidone), fillers (e.g. lactose, sugar, maize-starch, calcium phosphate, sorbitol or glycine), lubricants (e.g. magnesium stearate, talc, polyethylene glycol, or silica), disintegrants (e.g. starch) or wetting agents (e.g. sodium lauryl sulfate). Oral liquid preparations may be in the form of aqueous or oily suspensions, solutions, emulsions, syrups, elixers, etc. or may be presented as a dry product for reconstitution with water or other suitable vehicle before use. Such liquid preparations may contain conventional additives such as suspending agents, flavoring agents, diluents or emulsifying agents. For parenteral administration, inhalation or instillation, solutions or suspensions of a compound of formula I with conventional pharmaceutical vehicles may be employed, e.g. as an aerosol spray for inhalation, as an aqueous solution for intravenous injection or instillation, or as an oily suspension for intramuscular injection. The compounds may also be administered by means of inhalers or other devices which permit the active compounds in the form of dry powders to come into direct contact with the lungs.

The compounds of the present invention or pharmaceutical compositions thereof may be administered to human allergic patients in single oral doses of approximately 0.05–500 mg. of active ingredient and multiple oral doses totalling up to about 1000 mg./day of active ingredient. When administered by inhalation or instillation, lower doses are generally given, i.e. on the order of about 0.1 of the normal oral dosage for the particular compound in question. These values are illustrative only, however, and the physician of course will ultimately determine the dosage most suitable for a particular patient on the basis of factors such as age, weight, severity of the symptoms and the particular agent to be administered.

The in vivo animal model studies described below indicate that the compounds of formula I are highly potent antiallergy agents.

Biological Activity Data

The reagin-mediated rat Passive Cutaneous Anaphylaxis (PCA) screening test used to evaluate the present compounds is generally regarded as one of the best animal models for use in predicting the antiallergy activity of test compounds in man. Briefly, the method consists of passive sensitization of skin sites on the test animals with reaginic antibodies followed after 24 hours by administration of the test drug and antigen challenge. The allergic response is measured by use of Evans' blue dye and is evaluated by the spot diameter at the injection site. Details of the test are provided below.

Materials

Ovalbumin (5 times crystalline)
Dinitrobenzene sulfonic acid, $Na^+$ salt
*Bordetella pertussis* vaccine — phase I $10–20 \times 10^9$ killed organisms/ml.
Aluminum hydroxide gel — 10 mg./ml.
Potassium carbonate
Male Sprague-Dawley (S/D) Rats — 200 gms.

Female Sprague-Dawley Rats — 100 gms.
Tris Buffered Saline (TBS) — 0.02 M 2-amino-2-hydroxymethyl-1,3-propanediol (Tris), 0.15 M NaCl, pH 8.2

Antigen Preparation — DNP-d EA

A substituted ovalbumin antigen is used both as immunogen and challenging antigen. The antigen is prepared as follows: 500 mg. ovalbumin (EA) and 500 mg. $K_2CO_3$ are dissolved in 25 ml. distilled $H_2O$ and stirred at room temperature for 5 minutes. Five hundred (500) mg. dinitrobenzene sulfonic acid, $Na^+$ salt, (previously recrystallized from hot absolute ethanol) is then added slowly with continued stirring. The reaction mixture is then immediately placed in the dark and allowed to proceed for 2 hours with constant stirring. After 2 hours the mixture is placed in suitable dialysis tubing and dialyzed against 5 changes (4 liters each) of distilled $H_2O$ at 5° C. After dialysis the product is lyophilized and stored at room temperature in a brown or amber container. The antigen obtained will appear as a light yellow, amorphous solid which is very soluble in water or saline. It is designated as DNP denatured ovalbumin (DNP-d EA).

Immunization Method for IgE Production

Adult, male Sprague-Dawley rats are used as a source of reagin-rich antisera for the PCA model. Immunization is by a combination of DNP-d EA on $Al(OH)_3$ gel and *B. pertussis* vaccine. Preparation of the DNP-d EA-gel immunogen is as follows: Dissolve the DNP-d EA in TBS so as to give a concentration of 10 mg./ml. Slowly add 1 ml. of this solution to 10 ml. $Al(OH)_3$ gel (10 mg. solids/ml.) with constant stirring at room temperature. Stir the mixture an additional 30 minutes to insure a uniform adsorption of antigen on gel.

The resulting preparation is then used in combination with phase I *B. pertussis* vaccine to immunize male S/D rats as follows: For each rat administer 0.1 ml. DNP-d EA-gel suspension intramuscularly in each hind leg (200 μg DNP-d EA and 2 mg. gel total dose). Follow these injections by the intraperitoneal administration of 1.0 ml. *B. pertussis* vaccine (10–20 × $10^9$ organisms). The use of light ether anesthesia during this procedure is recommended to insure proper intramuscular and intraperitoneal injections. Nine days following immunization (but no longer than 10) the animals are exsanguinated by cardiac puncture or abdominal aorta cannulation under ether or pentobarbital anesthesia. The collected whole blood is allowed to clot, the serum separated by centrifugation and the individual serum samples stored frozen until assayed for IgE content.

Selection of High Titered Serum Samples for Pooling

Individual serum samples should be screened for reaginic antibody concentration before being pooled with other sera, as not all rats respond to immunization procedures with reagin production. A 1:50 saline dilution of serum from each immunized rat is used for this purpose. Intradermal injections of 0.05 ml. of the diluted sera are made in the shaven backs of two small female recipient rats, 100–120 gms. Several serum samples can be tested simultaneously in recipient animals. After a 24 to 48 hour latent period antigen challenge is accomplished by intravenous administration to each rat of 1 mg. DNP-d EA in 0.5 ml. of 0.5% Evans' blue dye in saline. Sera which show positive PCA reactions at the 1:50 dilution, as measured 20 to 30 minutes post-challenge are pooled, dispensed in small aliquots and stored at −70° C. or lower until used. Negative sera may be discarded.

The IgE titer of the antisera pool should then be determined. Serial two-fold dilutions (1:5 to 1:160) of unheated sera and sera heated at 56° C. for 1 hour are prepared in saline and 0.05 ml. of each dilution injected intradermally on the backs of female recipient rats. At least four animals should be used for both the heated and unheated serum titrations. After a 24-hour latent period each group is challenged with 1 mg. DNP-d EA in 0.5 ml. 0.5% Evans' blue dye. Reactions are read by reflecting the skin 20 to 30 minutes post-challenge. Intensity (blueing) and spot diameter should be measured and recorded. The pool titer is defined as the reciprocal of the greatest dilution of unheated serum which yields a measurable PCA response (>6 mm. diameter) in at least half of the recipient animals. Antiserum pools having a titer of 50 or greater are acceptable for the PCA screen. These pools should be sterile-filtered and stored at −70° C. or lower until use. Lyophilization in small aliquots may be used as an alternate.

PCA Screening Method

1. Animals—Young female Sprague-Dawley rats, 90–110 gms. should be used. The rats should be conditioned (acclimatized) for at least five days prior to use, with food and water ad lib.

2. Passive Sensitization—The test animals are prepared for passive sensitization by carefully shaving areas on each side of the back with a fine toothed clipper. Using a 27 gauge ⅜ inch needle mounted on a 1 ml. tuberculin syringe make intradermal injections of saline dilutions of the antiserum pool. Four dilutions (two on either side) of antiserum are used. The exact dilutions used depend on the titer of the pool. For example, if the antiserum pool has a titer of 50, then dilutions of 1:10, 1:20, 1:30 and 1:40 are used; if the pool titers at 100, then the dilutions would be 1:20, 1:40, 1:60 and 1:80. The sequence of placement of each dilution should be either clockwise or counter-clockwise to facilitate ease in scoring. The latent period should be at least 24 but no more than 48 hours.

3. Drug Administration-Standard and Unknowns—Four animals are used for each test compound. Disodium cromoglycate (DSCG), solubilized in saline, is administered by intravenous (i.v.) route at the time of antigen challenge. The tetrazole test compounds are solubilized in aqueous sodium bicarbonate. The test compounds are administered i.v. or per os (p.o.) either 1–5 or 10 minutes, respectively, prior to antigen challenge.

4. Antigen Challenge and Reaction Evaluation—Elicitation of the PCA response is accomplished by intravenous administration of 1 mg. DNP-d EA in 0.5 ml. 0.5% Evans' blue dye in saline to each test rat. PCA reactions are maximal 20 to 30 minutes post-challenge. Reactions should be scored visually for color intensity and the average diameter of the spots measured at each antiserum dilution site. Both operations should be done by reflecting the skin. For comparative purposes the numbers in the control group (untreated) should be at least 5% and usually 10%, of the total animals tested on a particular day.

Observed drug inhibition is reported as percent reduction in effective antiserum titer in treated versus control groups.

Results

Test results for certain of the preferred compounds of the present invention by i.v. and p.o. routes of administration are shown below in Table I along with data for DSCG. The results are given in terms of the $ID_{50}$ value, i.e. the dose of compound that inhibits 50% of the response.

Table I

Rat PCA Screening Data for 3-(1H-tetrazol-5-yl)-4H-pyrido[1,2-a]pyrimidin-4-ones Compound

| Example No. | $R^2$ | $R^3$ | $R^4$ | $ID_{50}$ in mg./kg. i.v. | p.o. |
|---|---|---|---|---|---|
| 1,2,3 | H | H | H | 0.06 | ~0.1 |
| 4 | $CH_3$ | H | H |  | ~0.1 |
| 5 | H | $CH_3$ | H |  | 2.4 |
| 6 | $CH_3CH_2$ | H | H |  | 0.04 |
| 7 | $CH_3(CH_2)_3$ | H | H |  | ~0.1 |
| 8 | $C_6H_5$ | H | H |  | 0.05 |
| 9 | Cl | H | H |  | ~0.07 |
| 10 | H | H | $CH_3$ |  | 0.0066 |
| 11 | $CH_3$ | H | $CH_3$ |  | 0.014 |
| 12 | H | H | $C_2H_5$ |  | ~0.0033 |
| DSCG | | | | ~0.6 | >>30 |

The following examples are provided solely for the purpose of illustrating preparation of the starting materials and compounds of the present invention and are not to be construed as limitations of the invention. All temperatures referred to below are in degrees Centigrade. "Skellysolve B" is a petroleum ether fraction of b.p. 60°–68° C. consisting essentially of n-hexane (trade name of Skelly Oil Co.).

PREPARATION OF STARTING MATERIALS

A. 2-Aminopyridines (general formula VII)

Preparation A1: 2-Amino-5-ethylpyridine a. Benzyl (5-Ethyl-2-pyridyl)carbamate

Diphenylphosphoryl azide (4.04 g., 14.7 mmoles) was added to a solution of 5-ethylpyridine-2-carboxylic acid (2.22 g., 14.7 mmoles), triethylamine (1.485 g., 14.7 mmoles), and benzyl alcohol (1.75 g., 16.17 mmoles) in 1,4-dioxane (23.5 ml.), and the mixture heated under reflux for one hour. The 1,4-dioxane was removed under reduced pressure. A solution of the residue in toluene was washed successively with water, aqueous sodium bicarbonate, and brine, and was then dried over sodium sulfate. The toluene was removed and the residue recrystallized from 2-propanol to give benzyl (5-ethyl-2-pyridyl)carbamate (1.9 g., 50.5%), m.p. 125°–127°. An analytical sample had m.p. 127°–130°.

Anal. Calcd for $C_{15}H_{16}N_2O_2$: C, 70.29; H, 6.29; N, 10.93. Found: C, 70.01; H, 6.32; N, 10.72.

b. 2-Amino-5-ethylpyridine

A suspension of benzyl (5-ethyl-2-pyridyl)carbamate (1.9 g., 7.43 mmoles) and 10% palladium-on-carbon (0.4 g.) in ethanol (100 ml.) was shaken with hydrogen at a pressure of 3.5 kg./cm² hours. The catalyst was removed by filtration and the filtrate concentrated to yield 2-amino-5-ethylpyridine (0.9 g., 99.4%) as a colorless oil.

Preparation A2: 2-Amino-5-n-butylpyridine a. Benzyl (5-n-Butyl-2-pyridyl)carbamate Diphenylphosphoryl azide (1.5 g., 5.58 mmoles) was added to a solution of 5-n-butylpyridine-2-carboxylic acid (1.0 g., 5.58 mmoles), triethylamine (0.565 g., 5.58 mmoles), and benzyl alcohol (0.663 g., 6.12 mmoles) in 1,4-dioxane (9.0 ml.) at 25°. The stirred solution was heated until an exothermic reaction began. When the exothermic reaction had subsided, the solution was heated under reflux for 1.5 hours. The reaction mixture was concentrated and the residue dissolved in toluene. This solution was washed successively with water, 10% aqueous sodium bicarbonate, and brine, and then dried over sodium sulfate. The solution was concentrated and the residue recrystallized from 2-propanol to give the title compound (0.91 g., 57%), m.p. 142°–143°.

Anal. Calcd for $C_{17}H_{20}N_2O_2$: C, 71.80; H, 7.09; N, 9.85. Found: C, 71.72; H, 6.85; N, 9.87.

b. 2-Amino-5-n-butylpyridine

A mixture of benzyl (5-n-butyl-2-pyridyl)carbamate (6.5 g. 22.86 mmoles) and 10% palladium on carbon (2.7 g.) in ethanol (400 ml.) was shaken at room temperature for 2 hours in an atmosphere of hydrogen at an initial pressure of 3.52 kg./cm.² The mixture was filtered and the filtrate reduced to dryness to leave 2-amino-5-n-butylpyridine (3.42 g., 99.7%), m.p. 30°–33° (lit. m.p. 35°–36° in *Helv. Chim. Acta*, 39, 505 (1956).

Preparation A3: 2-Amino-5-phenylpyridine

A solution of 2-chloro-5-phenylpyridine (4.0 g., 0.021 mole) in dry diethyl ether (160 ml.) was added dropwise to a solution of sodium (3.39 g., 0.15 g-atom) in liquid ammonia (160 ml.) containing ferrous nitrate hexahydrate (0.095 g.). The resulting suspension was allowed to reflux for 4 hours. Ammonium chloride was added and the ammonia allowed to evaporate. The residue was treated with 5% aqueous sodium hydroxide (5 ml.). The mixture was filtered. The aqueous layer was extracted with ether (2 × 100 ml.). The combined ethereal layers were washed with brine and dried over sodium sulfate. The solution was concentrated and the residue recrystallized from methylcyclohexane. The product was triturated with chloroform (100 ml.). The mixture was filtered and the filtrate evaporated to give 2-amino-5-phenylpyridine (1.3 g., 36%), m.p. 133°–135° (lit. m.p. 133° in *Chem. Ber.*, 91, 247 (1958).

Preparation A4: 2-Amino-3,5-dimethylpyridine

Ferrous nitrate hexahydrate (60 mg.) followed by sodium (4.5 g., 0.196 g-atom) were added to liquid ammonia. To this mixture was added a solution of 3,5-dimethylpyridine (10.0 g., 0.093 mole) in N,N-dimethylaniline (21 ml.) over a period of 5 minutes. The ammonia was allowed to evaporate and the residue heated under nitrogen by means of an oil bath maintained at 180° for 18 hours. The cooled residue was treated with ice (50 g.) followed by 2N sodium hydroxide (50 ml.). The mixture was triturated for 2 hours and then filtered. The collected solid was washed with boiling toluene (2 × 100 ml.). The toluene layer was separated from the combined filtrate and washings, concentrated to about 50 ml. and extracted with 5% aqueous acetic acid (5 × 20 ml.). The combined extracts were filtered and reduced to dryness. The residue was recrystallized from methylcyclohexane to give 2-amino-3,5-dimethylpyridine acetate (4.9 g., 29%), m.p. 85°–95°.

The acetate (2.5 g., 1.37 mmoles) was briefly suspended in 1N sodium hydroxide (50 ml.). The mixture was extracted with methylene chloride. The extract was washed with water, dried, and concentrated to give 2-amino-3,5-dimethylpyridine as an oil.

B. Carboxamide intermediates (general formula III)

Preparation B1: 4-Oxo-4H-pyrido[1,2-a]pyrimidine-3-carboxamide

A steel bomb containing ethyl 4-oxo-4H-pyrido-[1,2-a]pyrimidine-3-carboxylate (14.0 g., 0.064 mole) and liquid ammonia (ca. 55 ml.) was heated on a steam bath for 2 hours and then stored at 25° for 18 hours. The ammonia was removed to leave a solid which was recrystallized from 2-methoxyethanol to give the title compound (4.2 g., 34.6%), m.p. 266°–268° (lit. m.p. 264°–268° in *J. Chem. Soc.* (C), 2735 (1971).

Preparation B2: 7-Chloro-4-oxo-4H-pyrido[1,2-a]pyrimidine-3-carboxamide

A suspension of ethyl 7-chloro-4-oxo-4H-pyrido-[1,2-a]pyrimidine-3-carboxylate (9.7 g., 0.038 mole) in ammonium hydroxide (75 ml., sp gr 0.9) was triturated at room temperature for 18 hours. The mixture was filtered and the collected solid retriturated at room temperature in fresh ammonium hydroxide (100 ml., sp gr 0.9) for a further 18 hours. The solid material was collected by filtration, washed with cold water and dried to give the title compound (7.7 g., 90%) m.p. 281°–285°. A small sample was recrystallized from 2-methoxyethanol to give analytical material, m.p. 285°–287°.

Anal. Calcd for $C_9H_6ClN_3O_2$: C, 48.34; H, 2.70; Cl, 15.86; N, 18.79. Found: C, 48.54; H, 2.73; Cl, 15.46; N, 19.17.

C. Nitriles (general formula II)

Preparation C1: 4-Oxo-4H-pyrido[1,2-a]pyrimidine-3-carbonitrile

A mixture of 4-oxo-4H-pyrido[1,2-a]pyrimidine-3-carboxamide (3.6 g., 0.019 mole) and phosphorus oxychloride (50 ml.) was heated under reflux for 2 hours. The mixture was concentrated and the solid residue partitioned between methylene chloride and aqueous sodium carbonate. The methylene chloride layer was washed with water, dried, and concentrated. The residue was recrystallized from toluene to give the title compound (2.5 g., 76.8%), m.p. 219°–221°. Recrystallization from ethanol gave analytical material, m.p. 219°–220°. (lit. m.p. 208° in *J. Amer. Chem. Soc.*, 80, 3066 (1958).

Preparation C2: 7-Chloro-4-oxo-4H-pyrido[1,2-a]pyrimidine-3-carbonitrile

A suspension of 7-chloro-4-oxo-4H-pyrido[1,2-a]pyrimidine-3-carboxamide (7.55 g., 33.8 mmoles) in phosphorus oxychloride (200 ml.) was heated under reflux for 3.5 hours. The solution was concentrated. A solution of the residual solid in methylene chloride was added to ice water. The methylene chloride layer was concentrated and the residue recrystallized from 2-methoxymethanol to give the title compound (4.0 g., 57.6%), m.p. 239°–241°.

Anal. Calcd for $C_9H_4ClN_3O$: C, 52.57; H, 1.96; Cl, 17.25; N, 20.44. Found: C, 52.52; H, 2.08; Cl, 16.60; N, 20.32.

D. Acrylates (general formula VI)

Preparation D1: Ethyl 2-Cyano-3-(5-methyl-2-pyridylamino)acrylate

A mixture of 2-amino-5-methylpyridine (5.0 g., 46.2 mmoles) and ethyl ethoxymethylenecyanoacetate (7.82 g., 46.2 mmoles) was heated by means of an oil bath maintained at 100° for 15 minutes. The mixture was cooled and the resultant solid recrystallized from acetonitrile to give the title compound (5.4 g., 50.5%), m.p. 170°–171.5°.

Anal. Calcd. for $C_{12}H_{13}N_3O_2$: C, 62.32; H, 5.67; N, 18.17. Found: C, 62.44; H, 5.74; N, 18.05.

Preparation D2: Ethyl 2-Cyano-3-(5-ethyl-2-pyridylamino)acrylate

The title compound (m.p. 155°–156°, 25.4% yield) was prepared from 2-amino-5-ethylpyridine and ethyl ethoxymethylenecyanoacetate in a manner similar to that described for the preparation of ethyl 2-cyano-3-(5-methyl-2-pyridylamino)acrylate in Preparation D1.

Anal. Calcd. for $C_{13}H_{15}N_3O_2$: C, 63.66; H, 6.16; N, 17.13. Found: C, 63.54; H, 6.09; N, 17.02.

Preparation D3: Ethyl 2-Cyano-3-(5-n-butyl-2-pyridylamino)acrylate

A solution of 2-amino-5-n-butylpyridine (3.72 g., 23.43 mmoles) and ethyl ethoxymethylenecyanoacetate (3.96 g., 23.43 mmoles) in toluene was heated for 10 minutes by means of an oil bath maintained at 100°. The solution was cooled and treated with Skellysolve B (200 ml.). The mixture was triturated for 18 hours at room temperature and then filtered. The collected title compound (4.3 g., 67.2%) had m.p. 69°–73°.

Preparation D4: Ethyl 2-Cyano-3-(5-phenyl-2-pyridylamino)acrylate

A mixture of 2-amino-5-phenylpyridine (1.19 g., 6.99 mmoles) and ethyl ethoxymethylenecyanoacetate (1.18 g., 6.99 mmoles) was fused at an oil bath temperature of 100° for 15 minutes. The product was recrystallized from toluene to give the title compound (1.3 g.), m.p. 126°–134°. An additional crop of product (0.3 g.), m.p. 119°–126° was obtained from the mother liquors. Total yield of product, 1.6 g. (78%).

Preparation D5: Ethyl 2-Cyano-3-(3-methyl-2-pyridylamino)acrylate

A solution of 2-amino-3-methylpyridine (5.0 g., 0.0462 mole) and ethyl ethoxymethylenecyanoacetate (7.82 g., 0.0462 mole) in toluene (4 ml.) was heated for 15 minutes by means of an oil bath maintained at 100°. The solution was cooled and the title compound (9.1 g., 85%) collected by filtration. The product, m.p. 139°–143°, was recrystallized from 2-propanol to give an analytical sample, m.p. 144°–146°.

Anal. Calcd for $C_{12}H_{13}N_3O_2$: C, 62.32; H, 5.67; N, 18.17. Found: C, 61.87; H, 5.63; N, 18.42.

Preparation D6: Ethyl 2-Cyano-3-(3,5-dimethyl-2-pyridylamino)-acrylate

The title compound (79% yield), m.p. 156°–159° from methylcyclohexane, was prepared in a manner similar to that described for the preparation of ethyl 2-cyano-3-(3-methyl-2-pyridylamino)acrylate in Preparation D5.

Anal. Calcd for $C_{13}H_{15}N_3O_2$: C, 63.66; H, 6.16; N, 17.13. Found: C, 63.94; H, 6.24; N, 16.78.

Preparation D7: Ethyl 2-Cyano-3-(3-ethyl-2-pyridylamino)acrylate

A solution of 2-amino-3-ethylpyridine (13.0 g., 0.1063 mole) and ethyl ethoxymethylenecyanoacetate (18.0 g., 0.1063 mole) in toluene (50 ml.) was heated on a steam bath for 20 minutes. The solution was cooled and the mixture diluted with Skellysolve B. The mixture was filtered to give 19.0 g. of the title compound, m.p. 122°–125°. The filtrate was reduced to dryness and the residue recrystallized fromcyclohexane to give a further 7.0 g. of product, m.p. 122°–125° (total yield 99.6%). A portion of the second crop was recrystallized twice from methanol to give analytical material, m.p. 123°–125°.

Anal. Calcd for $C_{13}H_{15}N_3O_2$: C, 63.66; H, 6.16; N, 17.13. Found: C, 63.49; H, 6.18; N, 17.13.

EXAMPLE 1

3-(1H-Tetrazol-5-yl)-4H-pyrido[1,2-a]pyrimidin-4-one (via nitrile II)

A stirred mixture of 4-oxo-4H-pyrido[1,2-a]-pyrimidine-3-carbonitrile (2.17 g., 0.0127 mole), sodium azide (0.911 g., 0.014 mole), and ammonium chloride (0.75 g., 0.014 mole) in N,N-dimethylformamide (20 ml.) was heated by means of an oil bath maintained at 120° for 19 hours. The solvent was removed and the residue treated with hot aqueous sodium bicarbonate. The mixture was filtered. The filtrate was acidified with acetic acid. The precipitate was collected and recrystallized from acetic acid to give the title compound (0.52 g., 19%) m.p. 308°–309° (decomp). Recrystallization from acetic acid with charcoal treatment gave analytical material, m.p. 311°–312° (decomp).

Anal. Calcd for $C_9H_6N_6O$: C, 50.46; H, 2.82; N, 39.24. Found: C, 50.16; H, 2.81; N, 39.18.

EXAMPLE 2

3-(1H-Tetrazol-5-yl)-4H-pyrido[1,2-a]pyrimidin-4-one (via acrylate VI)

Aluminum chloride (0.74 g., 5.56 mmoles) was carefully added to tetrahydrofuran (33 ml.) at −20°. Sodium azide (1.08 g., 16.6 mmoles) was then added and the mixture heated under reflux for 30 minutes. After the addition of ethyl 2-cyano-3-(2-pyridylamino)acrylate (1.0 g., 4.6 mmoles) the mixture was again heated under reflux for 18 hours. The mixture was cooled in an ice bath, treated with water (170 ml.) and acidified to pH 2 with 6N hydrochloric acid. The resulting suspension was stirred with cooling for 2 hours and then filtered. The collected solid was recrystallized from N,N-dimethylformamide to give the title compound (0.38 g., 38.5%), m.p. 308°–309° (decomp).

EXAMPLE 3

3-(1H-tetrazol-5-yl)-4H-pyrido[1,2-a]pyrimidin-4-one (via 2-aminopyridine + ethoxymethylenecyanoacetate + Al (N$_3$)$_3$ without isolation of intermediates)

Aluminum chloride (1.73 g., 12.96 mmoles) was added to tetrahydrofuran (45 ml.) at −20°. Sodium azide (2.52 g., 38.71 mmoles) was then added and the mixture heated under reflux for 40 minutes. To this mixture was added 2-aminopyridine (1.0 g., 10.62 mmoles) and ethyl ethoxymethylenecyanoacetate (1.8 g., 10.62 mmoles). The mixture was heated under reflux for 18 hours. The mixture was concentrated and the residue treated with water (50 ml.). The mixture was acidified to pH 3 with 6N hydrochloric acid. The solid material was collected and suspended in 3% aqueous sodium bicarbonate. The mixture was heated under reflux for 5 minutes, filtered, and the filtrate acidified to pH 4 with 6N hydrochloric acid. The precipitate was recrystallized from N,N-dimethylformamide to give the title compound (0.35 g., 15.4%), m.p. 312°–313° (decomp).

EXAMPLE 4

7-Methyl-3-(1H-tetrazol-5-yl)-4H-pyrido[1,2-a]pyrimidin-4-one

In a manner similar to that described for the preparation of 3-(1H-tetrazol-5-yl)-4H-pyrido[1,2-a]pyrimidin-4-one in Example 2, the title compound was prepared from ethyl 2-cyano-3-(5-methyl-2-pyridylamino)acrylate. The product (42.8% yield) had m.p. 321°–322° (decomp) after recrystallization from glacial acetic acid.

Anal. Calcd for $C_{10}H_8N_6O$: C, 52.63; H, 3.53; N, 36.83. Found: C, 52.26; H, 3.40; N, 36.47.

EXAMPLE 5

8-Methyl-3-(1H-tetrazol-5-yl)-4H-pyrido[1,2-a]pyrimidin-4-one

The title compound (16% yield, m.p. 307° with decomposition) was prepared from ethyl 2-cyano-3-(4-methyl-2-pyridylamino)acrylate in a manner similar to that described for the preparation of 3-(1H-tetrazol-5-yl)-4H-pyrido[1,2-a]-pyrimidin-4-one in Example 2.

Anal. Calcd for $C_{10}H_8N_6O$: C, 52.63; H, 3.53; N, 36.83. Found: C, 52.57; H, 3.27; N, 36.92 (corrected for 2.7% $H_2O$).

Preparation of the starting material acrylate is disclosed in *J. Heterocycl. Chem.*, 8, 759 (1971).

EXAMPLE 6

7-Ethyl-3-(1H-tetrazol-5-yl)-4H-pyrido[1,2-a]pyrimidin-4-one

The title compound (28% yield, m.p. 289°–290.5° with decomposition) was prepared from ethyl 2-cyano-3-(5-ethyl-2-pyridylamino)acrylate in a manner similar to that described for the preparation of 3-(1H-tetrazol-5-yl)-4H-pyrido[1,2-a]pyrimidin-4-one in Example 2.

Anal. Calcd. for $C_{11}H_{10}N_6O$: C, 54.54; H, 4.16; N, 34.70. Found: C, 54.31; H, 4.09; N, 34.52.

EXAMPLE 7

7-n-Butyl-3-(1H-tetrazol-5-yl)-4H-pyrido[1,2-a]pyrimidin-4-one

Aluminum chloride (0.89 g., 6.67 mmoles was carefully added to cold (−30°) tetrahydrofuran (42 ml.). Sodium azide (1.3 g., 20.0 mmoles was then added and the mixture heated at reflux for 40 minutes. Ethyl 2-cyano-3-(5-n-butyl-2-pyridylamino)acrylate (1.50 g., 5.49 mmoles) was added and the mixture heated under reflux for 18 hours. The cooled mixture was concentrated and the residue treated with ice water (50 ml.). The mixture was acidified to pH 3 with 6N hydrochloric acid. The mixture was filtered and the collected solid treated with boiling 3% aqueous sodium bicarbonate for 10 minutes. The mixture was filtered and the filtrate acidified to pH 4 with 6N hydrochloric acid. The precipitate was recrystallized from N,N-dimethylformamide to give the title compound (0.45 g., 30.4%), m.p. 284°–285° (decomp).

Anal. Calcd. for $C_{13}H_{14}N_6O$: C, 57.76; H, 5.22; N, 31.10. Found: C, 57.37; H, 5.23; N, 31.21.

EXAMPLE 8

7-Phenyl-3-(1H-tetrazol-5-yl)-4H-pyrido[1,2-a]pyrimidin-4-one

In a manner similar to that described for the preparation of 7-n-butyl-3-(1H-tetrazol-5-yl)-4H-pyrido[1,2-a]pyrimidin-4-one in Example 7, the title compound (m.p. 308°–309° decomp) was prepared in 31% yield from ethyl 2-cyano-3-(5-phenyl-2-pyridylamino)acrylate.

Anal. Calcd. for $C_{15}H_{10}N_6O$: C, 62.06; H, 3.47; N, 28.95. Found: C, 61.93; H, 3.37; N, 28.67.

EXAMPLE 9

7-Chloro-3-(1H-tetrazol-5-yl)-4H-pyrido[1,2-a]pyrimidin-4-one

Aluminum chloride (0.72 g., 5.45 mmoles) was carefully added to cold (−30°) tetrahydrofuran (29 ml.). Sodium azide (1.06 g., 16.27 mmoles) was then added and the mixture heated under reflux for 30 minutes. 7-Chloro-4-oxo-4H-pyrido[1,2-a]pyrimidine-3-carbonitrile (1.0 g., 4.47 mmoles) was added and the mixture heated under reflux for 18 hours. The cooled mixture was poured onto 500 ml. of ice water and the resulting mixture acidified to pH 2 with 6N hydrochloric acid. The precipitate was collected and recrystallized from N,N-dimethylformamide to give the title compound (0.55 g., 49.5%), m.p. 300°–301° (decomp).

Anal. Calcd. for $C_9H_5ClN_6O$: C, 43.47; H, 2.03; Cl, 14.26; N, 33.80. Found: C, 43.63; H, 2.19; Cl, 13.74; N, 33.62.

EXAMPLE 10

9-Methyl-3-(1H-tetrazol-5-yl)-4H-pyrido[1,2-a]pyrimidin-4-one

Aluminum chloride (3.51 g., 0.0263 mole) was added to cold (−30°) tetrahydrofuran (180 ml.). Sodium azide (5.12 g., 0.0788 mole) was added and the mixture heated under reflux for 30 minutes. The mixture was cooled to 5°. Ethyl 2-cyano-3-(3-methyl-2-pyridylamino)acrylate (5.0 g., 0.0216 mole) was added and the mixture heated under reflux for 18 hours. The tetrahydrofuran was removed under reduced pressure. The residue was treated with ice water (100 ml.) and acidified to pH 3 with 6N hydrochloric acid. The mixture was filtered and the collected solid recrystallized from N,N-dimethylformamide to give the title compound (2.5 g., 50.7%), m.p. 310°–311° (decomp).

Anal. Calcd. for $C_{10}H_8N_6O$: C, 52.63; H, 3.53; N, 36.83. Found: C, 52.03; H, 3.51; N, 37.08.

EXAMPLE 11

7,9-Dimethyl-3-(1H-tetrazol-5-yl)-4H-pyrido[1,2-a]pyrimidin-4-one

The title compound (37.6% yield), m.p. 308°–309° (decomp) from 2-methoxyethanol, was prepared in a manner similar to that described for the preparation of 9-methyl-3-(1H-tetrazol-5-yl)-4H-pyrido[1,2-a]pyrimidin-4-one in Example 10.

Anal. Calcd. for $C_{11}H_{10}N_6O$: C, 54.54; H, 4.16; N, 34.70. Found: C, 54.09; H, 4.10; N, 35.29.

EXAMPLE 12

9-Ethyl-3-(1H-tetrazol-5-yl)-4H-pyrido[1,2-a]pyrimidin-4-one

Ethyl 2-cyano-3-(3-ethyl-2-pyridylamino)acrylate (10.0 g., 0.0408 mole) was added to a stirred mixture of aluminum azide in tetrahydrofuran at 0°. The aluminum azide had been prepared in situ in the usual manner from aluminum chloride (6.5 g., 0.0488 mole) and sodium azide (9.5 g., 0.1464 mole) in tetrahydrofuran (100 ml.). The mixture was stirred at 0° for 15 minutes and then heated under reflux for 19 hours. The mixture was cooled, diluted with water, and acidified with concentrated hydrochloric acid (20 ml.). The mixture was filtered to give the title compound (2.7 g., 27%), m.p. 285°–288°. The product was recrystallized from N,N-dimethylformamide with charcoal treatment to give analytical material, m.p. 288°–290° (decomp).

Anal. Calcd. for $C_{11}H_{10}N_6O$: C, 54.54; H, 4.16; N, 34.70. Found: C, 54.70; H, 4.17; N, 35.27.

EXAMPLE 13

Following the general procedures of Examples 1–12, the following compounds may be prepared by use of the appropriate 2-aminopyridine starting material.

| $R^1$ | $R^2$ | $R^3$ | $R^4$ |
|---|---|---|---|
| CH₃ | H | H | H |
| H | CO₂H | H | H |
| H | NO₂ | H | H |
| H | ᵃNH₂ | H | H |
| H | H | H | CH₃O |
| H | H | H | CH₃OCH₂CH₂ |
| H | H | H | Cl |
| H | H | H | (CH₃)₂CH |
| H | C₂H₅ | H | C₂H₅ |
| H | NO₂ | H | CH₃ |
| H | H | H | ᵇOH |
| H | H | H | HOCH₂ |
| H | H | CH₃ | CH₃ |
| H | Cl | H | Cl |
| H | H | H | C₆H₅ |
| H | H | H | C₆H₅CH₂ |
| H | H | H | p-chlorophenyl |
| H | H | H | o-methylphenyl |
| H | H | H | o-ethylphenyl |
| H | H | H | m-methoxyphenyl |
| H | H | H | p-ethoxyphenyl |
| H | H | H | o-bromophenyl |
| H | H | H | 3-chloro-4-methylphenyl |
| H | H | H | 3,4-dimethoxyphenyl |
| H | C₆H₅CH₂ | H | H |
| H | p-chlorophenyl | H | H |
| CH₃O | H | H | H |
| H | Br | H | H |
| H | Br | H | Br |
| C₂H₅O | H | H | H |
| H | H | Cl | H |
| Br | H | H | H |
| CH₃ | H | CH₃ | H |
| H | ᵇOH | H | H |
| H | CH₃SO | H | H |
| H | H | H | NO₂ |
| H | n-C₃H₇ | H | H |
| H | CH₂=CHCH₂ | H | H |
| H | CH≡CCH₂ | H | H |
| H | (CH₃)₂CH | H | H |
| H | (CH₃)₃C | H | H |
| H | (CH₃)₃CHCH₂ | H | H |
| H | C₂H₅CH(CH₃) | H | H |
| H | H | H | n-C₃H₇ |
| H | H | H | n-C₄H₉ |
| H | H | H | (CH₃)₂CHCH₂ |

-continued

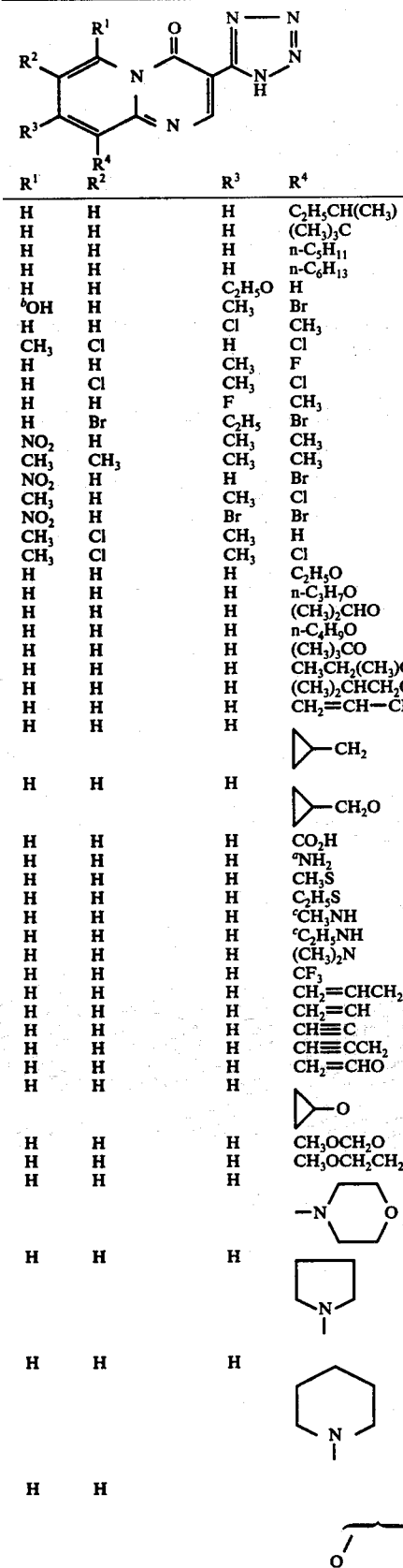

| R¹ | R² | R³ | R⁴ |
|---|---|---|---|
| H | H | H | C₂H₅CH(CH₃) |
| H | H | H | (CH₃)₃C |
| H | H | H | n-C₅H₁₁ |
| H | H | H | n-C₆H₁₃ |
| H | H | C₂H₅O | H |
| ᵇOH | H | CH₃ | Br |
| H | H | Cl | CH₃ |
| CH₃ | Cl | H | Cl |
| H | H | CH₃ | F |
| H | Cl | CH₃ | Cl |
| H | H | F | CH₃ |
| H | Br | C₂H₅ | Br |
| NO₂ | H | CH₃ | CH₃ |
| CH₃ | CH₃ | CH₃ | CH₃ |
| NO₂ | H | H | Br |
| CH₃ | H | CH₃ | Cl |
| NO₂ | H | Br | Br |
| CH₃ | Cl | CH₃ | H |
| CH₃ | Cl | CH₃ | Cl |
| H | H | H | C₂H₅O |
| H | H | H | n-C₃H₇O |
| H | H | H | (CH₃)₂CHO |
| H | H | H | n-C₄H₉O |
| H | H | H | (CH₃)₃CO |
| H | H | H | CH₃CH₂(CH₃)CHO |
| H | H | H | (CH₃)₂CHCH₂O |
| H | H | H | CH₂=CH—CH₂O |
| H | H | H | ▷—CH₂ |
| H | H | H | ▷—CH₂O |
| H | H | H | CO₂H |
| H | H | H | ᵃNH₂ |
| H | H | H | CH₃S |
| H | H | H | C₂H₅S |
| H | H | H | ᶜCH₃NH |
| H | H | H | ᶜC₂H₅NH |
| H | H | H | (CH₃)₂N |
| H | H | H | CF₃ |
| H | H | H | CH₂=CHCH₂ |
| H | H | H | CH₂=CH |
| H | H | H | CH≡C |
| H | H | H | CH≡CCH₂ |
| H | H | H | CH₂=CHO |
| H | H | H | ▷—O |
| H | H | H | CH₃OCH₂O |
| H | H | H | CH₃OCH₂CH₂O |
| H | H | H | —N(morpholino) |
| H | H | H | (pyrrolidinyl) |
| H | H | H | (piperidinyl) |
| H | H | H | (1,3-dioxolanyl-CH₂) |

-continued

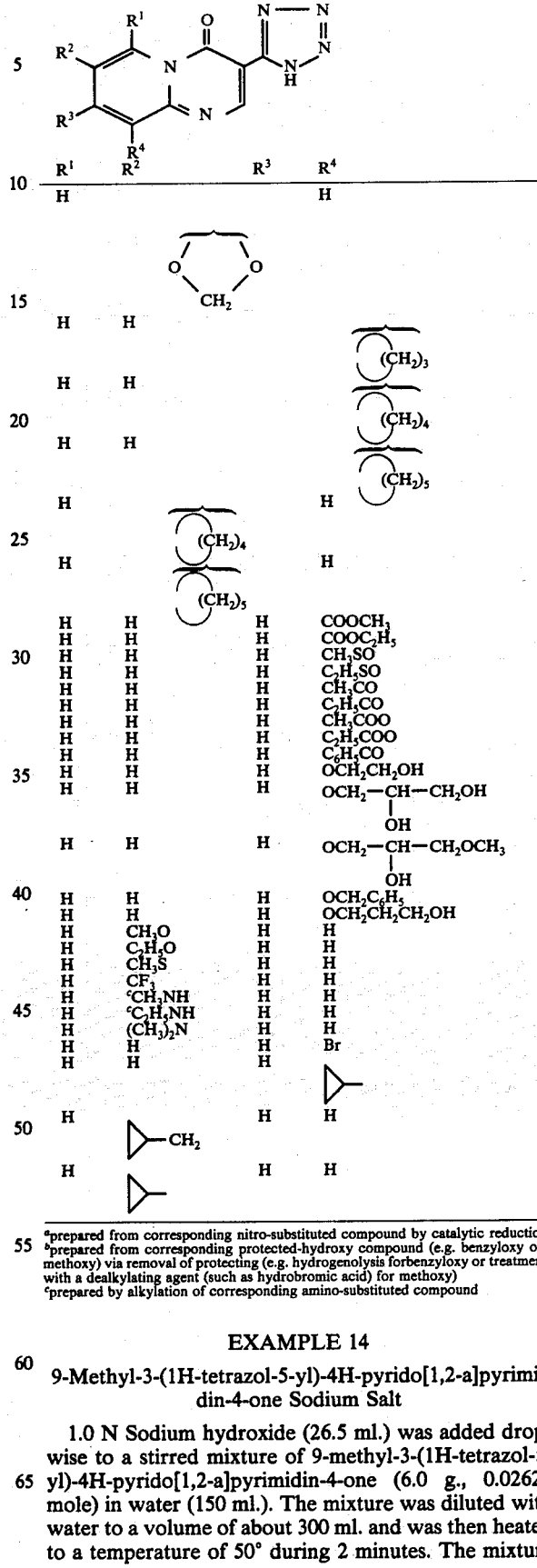

| R¹ | R² | R³ | R⁴ |
|---|---|---|---|
| H | H | H | H |
| H | H | H | (1,3-dioxolanyl-CH₂) |
| H | H | (CH₂)₃ bridge | |
| H | H | (CH₂)₄ bridge | |
| H | H | (CH₂)₅ bridge | H |
| H | (CH₂)₄ bridge | | H |
| H | (CH₂)₅ bridge | | H |
| H | H | H | COOCH₃ |
| H | H | H | COOC₂H₅ |
| H | H | H | CH₃SO |
| H | H | H | C₂H₅SO |
| H | H | H | CH₃CO |
| H | H | H | C₂H₅CO |
| H | H | H | CH₃COO |
| H | H | H | C₂H₅COO |
| H | H | H | C₆H₅CO |
| H | H | H | OCH₂CH₂OH |
| H | H | H | OCH₂—CH—CH₂OH<br>　　　　　│<br>　　　　　OH |
| H | H | H | OCH₂—CH—CH₂OCH₃<br>　　　　　│<br>　　　　　OH |
| H | H | H | OCH₂C₆H₅ |
| H | H | H | OCH₂CH₂CH₂OH |
| H | CH₃O | H | H |
| H | C₂H₅O | H | H |
| H | CH₃S | H | H |
| H | CF₃ | H | H |
| H | ᶜCH₃NH | H | H |
| H | ᶜC₂H₅NH | H | H |
| H | (CH₃)₂N | H | H |
| H | H | H | H |
| H | H | H | Br |
| H | H | H | ▷ |
| H | H | H | ▷—CH₂ |
| H | H | H | ▷ |

ᵃprepared from corresponding nitro-substituted compound by catalytic reduction
ᵇprepared from corresponding protected-hydroxy compound (e.g. benzyloxy or methoxy) via removal of protecting (e.g. hydrogenolysis for benzyloxy or treatment with a dealkylating agent (such as hydrobromic acid) for methoxy)
ᶜprepared by alkylation of corresponding amino-substituted compound

EXAMPLE 14

9-Methyl-3-(1H-tetrazol-5-yl)-4H-pyrido[1,2-a]pyrimidin-4-one Sodium Salt 1.0 N Sodium hydroxide (26.5 ml.) was added dropwise to a stirred mixture of 9-methyl-3-(1H-tetrazol-5-yl)-4H-pyrido[1,2-a]pyrimidin-4-one (6.0 g., 0.02625 mole) in water (150 ml.). The mixture was diluted with water to a volume of about 300 ml. and was then heated to a temperature of 50° during 2 minutes. The mixture was filtered and the water removed from the filtrate by lyophilization. The residue was recrystallized from water:ethanol to give the title compound (5.4 g.), m.p. 346° (decomp). Elemental analyses were performed on the product after it had been stored at 22° for 66 hours at a relative humidity of 50–55%.

Anal. Calcd. for $C_{10}H_7NaN_6O$: C, 48.01; H, 2.82. Found: C, 47.91; H, 2.78 (corrected for 9.01% $H_2O$).

Replacement of the 9-methyl-3-(1H-tetrazol-5-yl)-4H-pyrido[1,2-a]pyrimidin-4-one in the above procedure with an equimolar weight of the other 3-(1H-tetrazol-5-yl)-4H-pyrido[1,2-a]pyrimidin-4-one compounds prepared in Examples 1–13 above gives the corresponding sodium salts for each of the indicated compounds.

Replacement of the sodium hydroxide in the above procedure with other bases, e.g. KOH, $Ca(OH)_2$, $Mg(OH)_2$ or $NH_4OH$ gives the corresponding base addition salts.

Reaction of the 3-(1H-tetrazol-5-yl)-4H-pyrido[1,2-a]pyrimidin-4-one compounds of Examples 1–13 with an equivalent weight of ethanolamine, ethylenediamine, diethanolamine, triethanolamine or tris(hydroxymethyl)aminomethane gives the corresponding amine salts for each of the indicated compounds.

The 3-(1H-tetrazol-5-yl)-4H-pyrido[1,2-a]pyrimidin-4-one compounds of Examples 1–13 may be converted to their acid addition salts by addition of a stoichiometric equivalent of a suitable organic or inorganic acid, e.g. HCl, HBr, HI, $H_3PO_4$ or $CH_3COOH$.

We claim:

1. A compound of the formula

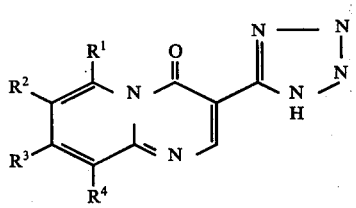

wherein $R^1$, $R^2$, $R^3$ and $R^4$ which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O—(lower)alkenyl,

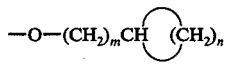

in which m is 0 or an integer from 1 to 6 and n is an integer from 2 to 7, $-OCH_2(CH_2)_xO(CH_2)_yCH_3$ in which x and y are each independently 0 or an integer from 1 to 6, $CF_3$, hydroxy, hydroxymethyl, (lower)alkylthio, amino, nitro,

in which r is 4 or 5 (lower)alkylamino, di(lower)alkylamino, carboxyl, $-CO_2$-(lower)alkyl, phenyl, phenyl substituted by one or two (lower)alkyl, (lower)alkoxy or halogen radicals, benzyl, (lower)alkylsulfinyl, $R^c$—CO— in which $R^c$ is (lower)alkyl, $R^c$—COO— in which $R^c$ is (lower)alkyl, $-O(CH_2)_kOH$ in which k is an integer from 2 to 6,

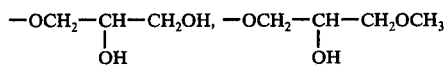

or $-OCH_2C_6H_5$, or a pharmaceutically acceptable salt thereof, with the provisos that (1) when two or more of $R^1$, $R^2$, $R^3$ and $R^4$ are tertiary alkyl groups, they are located on non-adjacent positions and (2) no more than two of $R^1$, $R^2$, $R^3$ and $R^4$ may be nitro groups.

2. A compound of claim 1 wherein $R^1$, $R^2$, $R^3$ and $R^4$ which may be the same or different are each hydrogen, (lower)alkyl, (lower)alkenyl, (lower)alkoxy, hydroxy, carboxy, (lower)alkylthio, halogen, $CF_3$, amino, (lower)alkylamino, di(lower)alkylamino, phenyl or benzyl.

3. A compound of the formula

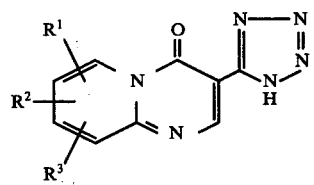

wherein $R^1$, $R^2$ and $R^3$ which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O-(lower)alkenyl,

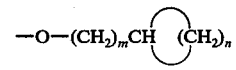

in which m is 0 or an integer from 1 to 6 and n is an integer from 2 to 7, $-OCH_2(CH_2)_xO(CH_2)_yCH_3$ in which x and y are each independently 0 or an integer from 1 to 6, $CF_3$, hydroxy, hydroxymethyl, (lower)alkylthio, amino, nitro,

in which r is 4 or 5, (lower)alkylamino, di(lower)alkylamino, carboxyl, $-CO_2$-(lower)alkyl, phenyl, phenyl substituted by one or two (lower)alkyl, (lower)alkoxy or halogen radicals, benzyl, (lower)alkylsulfinyl, $R^c$—CO— in which $R^c$ is (lower)alkyl, $R^c$—COO— in which $R^c$ is (lower)alkyl, $-O(CH_2)_kOH$ in which k is an integer from 2 to 6,

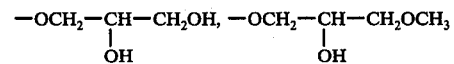

or $-OCH_2C_6H_5$, or a pharmaceutically acceptable salt thereof, with the provisos that (1) when two or more of $R^1$, $R^2$ and $R^3$ are tertiary alkyl groups, they are located on non-adjacent positions and (2) no more than two of $R^1$, $R^2$ and $R^3$ may be nitro groups.

4. A compound of claim 3 wherein $R^1$, $R^2$ and $R^3$ are each independently hydrogen, (lower)alkyl, (lower)alkenyl, (lower)alkoxy, hydroxy, carboxy, (lower)alkylthio, halogen, $CF_3$, amino, (lower)alkylamino, di(lower)alkylamino, phenyl or benzyl.

5. A compound of the formula

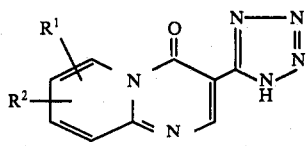

wherein R¹ and R² which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O-(lower)alkenyl,

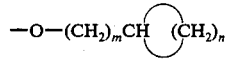

in which m is 0 or an integer from 1 to 6 and n is an integer from 2 to 7, —OCH₂(CH₂)ₓO(CH₂)ᵧCH₃ in which x and y are each independently 0 or an integer from 1 to 6, CF₃, hydroxy, hydroxymethyl, (lower)alkylthio, amino, nitro,

in which r is 4 or 5, (lower)alkylamino, di(lower)alkylamino, carboxyl, —CO₂-(lower)alkyl, phenyl, phenyl substituted by one or two (lower)alkyl, (lower)alkoxy or halogen radicals, benzyl, (lower)alkylsulfinyl, Rᶜ—CO— in which Rᶜ is (lower)alkyl, Rᶜ—COO— in which Rᶜ is (lower)alkyl, —O(CH₂)ₖOH in which k is an integer from 2 to 6,

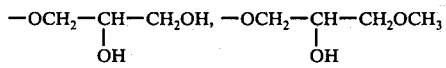

or —OCH₂C₆H₅, or a pharmaceutically acceptable salt thereof, with the proviso that when R¹ and R² are both tertiary alkyl groups, they are located on non-adjacent positions.

6. A compound of claim 5 wherein R¹ and R² are each independently hydrogen, (lower)alkyl, (lower)alkenyl, (lower)alkoxy, hydroxy, carboxy, (lower)alkylthio, halogen, CF₃, amino, (lower)alkylamino, di(lower)alkylamino, phenyl or benzyl.

7. A compound of the formula

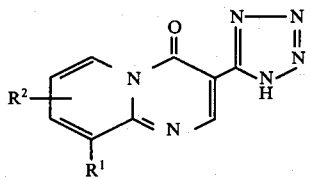

wherein R¹ and R² which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O-(lower)alkenyl,

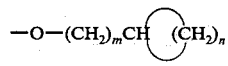

in which m is 0 or an integer from 1 to 6 and n is an integer from 2 to 7, —OCH₂(CH₂)ₓO(CH₂)ᵧCH₃ in which x and y are each independently 0 or an integer from 1 to 6, CF₃, hydroxy, hydroxymethyl, (lower)alkylthio, amino, nitro,

in which R is 4 or 5, (lower)alkylamino, di(lower)alkylamino, carboxyl, —CO₂-(lower)alkyl, phenyl, phenyl substituted by one or two (lower)alkyl, (lower)alkoxy or halogen radicals, benzyl, (lower)alkylsulfinyl, Rᶜ—CO— in which Rᶜ is (lower)alkyl, Rᶜ—COO— in which Rᶜ is (lower)alkyl, —O(CH₂)ₖOH in which k is an integer from 2 to 6,

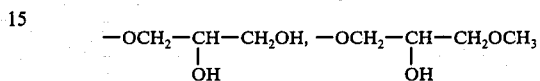

or —OCH₂C₆H₅, or a pharmaceutically acceptable salt thereof, with the proviso that when R¹ and R² are both tertiary alkyl groups, they are located on non-adjacent positions.

8. A compound of claim 7 wherein R¹ and R² are each independently hydrogen, (lower)alkyl, (lower)alkenyl, (lower)alkoxy, hydroxy, carboxy, (lower)alkylthio, halogen, CF₃, amino, (lower)alkylamino, di(lower)alkylamino, phenyl or benzyl.

9. A compound of the formula

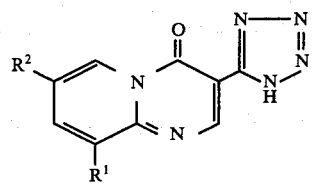

wherein R¹ and R² which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O-(lower)alkenyl,

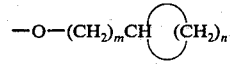

in which m is 0 or an integer from 1 to 6 and n is an integer from 2 to 7, —OCH₂(CH₂)ₓO(CH₂)ᵧCH₃ in which x and y are each independently 0 or an integer from 1 to 6, CF₃, hydroxy, hydroxymethyl, (lower)alkylthio, amino, nitro,

in which r is 4 or 5, (lower)alkylamino, di(lower)alkylamino, carboxyl, —CO₂-(lower)alkyl, phenyl, phenyl substituted by one or two (lower)alkyl, (lower)alkoxy or halogen radicals, benzyl, (lower)alkylsulfinyl, Rᶜ—CO— in which Rᶜ is (lower)alkyl, Rᶜ—COO— in which Rᶜ is (lower)alkyl, —O(CH₂)ₖOH in which k is an integer from 2 to 6,

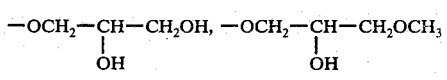

or —OCH₂C₆H₅, or a pharmaceutically acceptable salt thereof.

10. A compound of claim 9 wherein R¹ and R² are each independently hydrogen, (lower)alkyl, (lower)alkenyl, (lower)alkoxy, hydroxy, carboxy, (lower)alkylthio, halogen, CF₃, amino, (lower)alkylamino, di(lower)alkylamino, phenyl or benzyl.

11. The compound of claim 9 named 7,9-dimethyl-3-(1H-tetrazol-5-yl)-4H-pyrido[1,2-a]pyrimidin-4-one, or a pharmaceutically acceptable salt thereof.

12. A compound of the formula

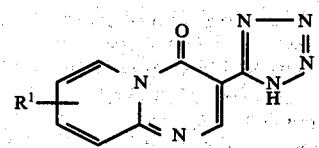

wherein R¹ is hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O—(lower)alkenyl,

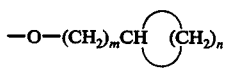

in which m is 0 or an integer from 1 to 6 and n is an integer from 2 to 7, —OCH₂(CH₂)ₓO(CH₂)ᵧCH₃ in which x and y are each independently 0 or an integer from 1 to 6, CF₃, hydroxy, hydroxymethyl, (lower)alkylthio, amino, nitro,

in which r is 4 or 5, (lower)alkylamino, di(lower)alkylamino, carboxyl, —CO₂—(lower)alkyl, phenyl, phenyl substituted by one or two (lower)alkyl, (lower)alkoxy or halogen radicals, benzyl, (lower)alkylsulfinyl, Rᶜ—CO— in which Rᶜ is (lower)alkyl, Rᶜ—COO— in which Rᶜ is (lower)alkyl, —O(CH₂)ₖOH in which k is an integer from 2 to 6,

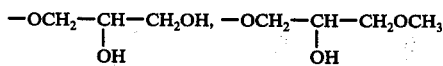

or —OCH₂C₆H₅, or a pharmaceutically acceptable salt thereof.

13. A compound of claim 12 wherein R¹ is hydrogen, (lower)alkyl, (lower)alkenyl, (lower)alkoxy, hydroxy, carboxy, (lower)alkylthio, halogen, CF₃, amino, (lower)alkylamino, di(lower)alkylamino, phenyl or benzyl.

14. The compound of claim 12 named 8-methyl-3-(1H-tetrazol-5-yl)-4H-pyrido[1,2-a]pyrimidin-4-one, or a pharmaceutically acceptable salt thereof.

15. A compound of the formula

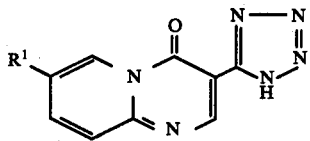

wherein R¹ is hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O—(lower)alkenyl,

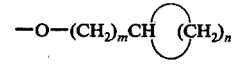

in which m is 0 or an integer from 1 to 6 and n is an integer from 2 to 7, —OCH₂(CH₂)ₓO(CH₂)ᵧCH₃ in which x and y are each independently 0 or an integer from 1 to 6, CF₃, hydroxy, hydroxymethyl, (lower)alkylthio, amino, nitro,

in which r is 4 or 5, (lower)alkylamino, di(lower)alkylamino, carboxyl, —CO₂—(lower)alkyl, phenyl, phenyl substituted by one or two (lower)alkyl, (lower)alkoxy or halogen radicals, benzyl, (lower)alkylsulfinyl, Rᶜ—CO— in which Rᶜ is (lower)alkyl, Rᶜ—COO— in which Rᶜ is (lower)alkyl, —O(CH₂)ₖOH in which k is an integer from 2 to 6,

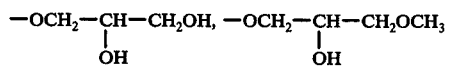

or —OCH₂C₆H₅, or a pharmaceutically acceptable salt thereof.

16. A compound of claim 15 wherein R¹ is hydrogen, (lower)alkyl, (lower)alkenyl, (lower)alkoxy, hydroxy, carboxy, (lower)alkylthio, halogen, CF₃, amino, (lower)alkylamino, di(lower)alkylamino, phenyl or benzyl.

17. The compound of claim 15 named 7-methyl-3-(1H-tetrazol-5-yl)-4H-pyrido[1,2-a]pyrimidin-4-one, or a pharmaceutically acceptable salt thereof.

18. The compound of claim 15 named 7-ethyl-3-(1H-tetrazol-5-yl)-4H-pyrido[1,2-a]pyrimidin-4-one, or a pharmaceutically acceptable salt thereof.

19. The compound of claim 15 named 7-n-butyl-3-(1H-tetrazol-5-yl)-4H-pyrido[1,2-a]pyrimidin-4-one, or a pharmaceutically acceptable salt thereof.

20. The compound of claim 15 named 7-phenyl-3-(1H-tetrazol-5-yl)-4H-pyrido[1,2-a]pyrimidin-4-one, or a pharmaceutically acceptable salt thereof.

21. The compound of claim 15 named 7-chloro-3-(1H-tetrazol-5-yl)-4H-pyrido[1,2-a]pyrimidin-4-one, or a pharmaceutically acceptable salt thereof.

22. A compound of the formula

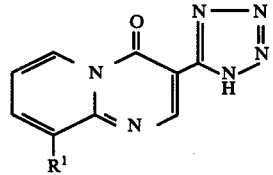

wherein R¹ is hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O—(lower)alkenyl,

in which m is 0 or an integer from 1 to 6 and n is an integer from 2 to 7, —OCH₂CCH₂)ₓO(CH₂)ᵧCH₃ in which $x$ and $y$ are each independently 0 or an integer from 1 to 6, $CF_3$, hydroxy, hydroxymethyl, (lower)alkylthio, amino, nitro,

in which $r$ is 4 or 5, (lower)alkylamino, di(lower)alkylamino, carboxyl, —$CO_2$—(lower)alkyl, phenyl, phenyl substituted by one or two (lower)alkyl, (lower)alkoxy or halogen radicals, benzyl, (lower)alkylsulfinyl, $R^c$—CO— in which $R^c$ is (lower)alkyl, $R^c$—COO— in which $R^c$ is (lower)alkyl, —$O(CH_2)_kOH$ in which $k$ is an integer from 2 to 6,

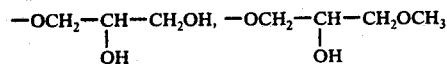

or —$OCH_2C_6H_5$, or a pharmaceutically acceptable salt thereof.

23. A compound of claim 22 wherein $R^1$ is hydrogen, (lower)alkyl, (lower)alkenyl, (lower)alkoxy, hydroxy, carboxy, (lower)alkylthio, halogen, $CF_3$, amino, (lower)alkylamino, di(lower)alkylamino, phenyl or benzyl.

24. The compound of claim 22 named 9-methyl-3-(1H-tetrazol-5-yl)-4H-pyrido[1,2-a]pyrimidin-4-one, or a pharmaceutically acceptable salt thereof.

25. The sodium salt of the compound of claim 24.

26. The compound of claim 22 named 3-(1H-tetrazol-5-yl)-4H-pyrido[1,2-a]pyrimidin-4-one, or a pharmaceutically acceptable salt thereof.

27. The compound of claim 22 named 9-ethyl-3-(1H-tetrazol-5-yl)-4H-pyrido[1,2-a]pyrimidin-4-one, or a pharmaceutically acceptable salt thereof.

* * * * *

UNITED STATES PATENT AND TRADEMARK OFFICE
CERTIFICATE OF CORRECTION

PATENT NO. : 4,122,274
DATED : October 24, 1978
INVENTOR(S) : Peter Frederick Juby It is certified that error appears in the above-identified patent and that said Letters Patent are hereby corrected as shown below:

In Claim 1, lines 35-39, tetrazolyl moiety of structural formula should read

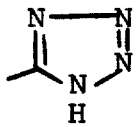

In Claim 22, line 68, "$-OCH_2CCH_2)_xO(CH_2)_yCH_3$" should read -- $-OCH_2(CH_2)_xO(CH_2)_yCH_3$ --.

Signed and Sealed this

Twenty-seventh Day of February 1979

[SEAL]

Attest:

RUTH C. MASON
Attesting Officer

DONALD W. BANNER
Commissioner of Patents and Trademarks